US010058078B2

(12) United States Patent
Carlson et al.

(10) Patent No.: US 10,058,078 B2
(45) Date of Patent: Aug. 28, 2018

(54) PRODUCTION OF FMDV-RESISTANT LIVESTOCK BY ALLELE SUBSTITUTION

(71) Applicant: Recombinetics, Inc., Saint Paul, MN (US)

(72) Inventors: Daniel F. Carlson, Inver Grove Heights, MN (US); Scott C. Fahrenkrug, Minneapolis, MN (US)

(73) Assignee: RECOMBINETICS, INC., Saint Paul, MN (US)

( * ) Notice: Subject to any disclaimer, the term of this patent is extended or adjusted under 35 U.S.C. 154(b) by 0 days.

(21) Appl. No.: 13/836,860

(22) Filed: Mar. 15, 2013

(65) Prior Publication Data
US 2014/0041066 A1 Feb. 6, 2014

Related U.S. Application Data

(60) Provisional application No. 61/677,904, filed on Jul. 31, 2012.

(51) Int. Cl.
A01K 67/027 (2006.01)
C07K 14/47 (2006.01)

(52) U.S. Cl.
CPC .......... A01K 67/0275 (2013.01); C07K 14/47 (2013.01); A01K 2217/05 (2013.01); A01K 2227/101 (2013.01); A01K 2227/108 (2013.01); A01K 2267/02 (2013.01)

(58) Field of Classification Search
CPC ............ A01K 67/0275; A01K 2217/05; A01K 2227/101; A01K 2227/108; A01K 2267/02
See application file for complete search history.

(56) References Cited

U.S. PATENT DOCUMENTS

| | | | |
|---|---|---|---|
| 4,873,191 A | 10/1989 | Wilkins | |
| 4,888,274 A | 12/1989 | Radding et al. | |
| 5,610,053 A | 3/1997 | Chung et al. | |
| 5,731,178 A | 3/1998 | Sippel et al. | |
| 5,763,240 A | 6/1998 | Zarling et al. | |
| 5,948,653 A | 9/1999 | Pati et al. | |
| 6,100,448 A | 8/2000 | Thompson et al. | |
| 6,180,385 B1 | 1/2001 | Skern et al. | |
| 6,395,549 B1 | 5/2002 | Tuan et al. | |
| 6,541,684 B1 | 4/2003 | Bowen et al. | |
| 6,548,741 B2 | 4/2003 | DeSousa et al. | |
| 6,613,752 B2 | 9/2003 | Kay et al. | |
| 6,720,478 B1 | 4/2004 | Mahajan et al. | |
| 6,905,857 B2 | 6/2005 | Bowen et al. | |
| 7,034,117 B2 | 4/2006 | Mahajan et al. | |
| 7,199,281 B2 | 4/2007 | Murray et al. | |
| 7,361,641 B2 | 4/2008 | Calos | |
| 7,709,206 B2 | 5/2010 | DeNise et al. | |
| 8,106,255 B2 | 1/2012 | Carroll et al. | |
| 8,586,526 B2 | 11/2013 | Gregory et al. | |
| 2001/0016315 A1 | 8/2001 | Renaville et al. | |
| 2003/0232410 A1 | 12/2003 | Lijedahl et al. | |
| 2004/0203158 A1 | 10/2004 | Hackett et al. | |
| 2005/0003542 A1 | 1/2005 | Kay et al. | |
| 2005/0153317 A1 | 7/2005 | DeNise et al. | |
| 2010/0105140 A1 | 4/2010 | Fahrenkrug et al. | |
| 2010/0138939 A1 | 6/2010 | Bentzon et al. | |
| 2010/0146655 A1 | 6/2010 | Fahrenkrug et al. | |
| 2010/0251395 A1 | 9/2010 | Harris et al. | |
| 2011/0023140 A1 | 1/2011 | Bedell et al. | |
| 2011/0023159 A1 | 1/2011 | Bedell et al. | |
| 2011/0059160 A1 | 3/2011 | Essner et al. | |
| 2011/0197290 A1 | 8/2011 | Fahrenkrug et al. | |
| 2011/0201118 A1 | 8/2011 | Yang et al. | |
| 2011/0207221 A1 | 8/2011 | Cost et al. | |
| 2011/0281306 A1 | 11/2011 | Kim et al. | |
| 2011/0287545 A1 | 11/2011 | Cost et al. | |
| 2011/0301073 A1 | 12/2011 | Gregory et al. | |
| 2012/0149115 A1 | 6/2012 | Kim et al. | |
| 2012/0192298 A1 | 7/2012 | Weinstein et al. | |
| 2012/0196370 A1 | 8/2012 | Urnov et al. | |
| 2012/0220037 A1 | 8/2012 | Fahrenkrug et al. | |
| 2012/0222143 A1 | 8/2012 | Fahrenkrug et al. | |
| 2013/0117870 A1 | 5/2013 | Fahrenkrug et al. | |
| 2013/0198878 A1 | 8/2013 | Doyon et al. | |
| 2013/0212725 A1 | 8/2013 | Kuhn et al. | |
| 2013/0217131 A1 | 8/2013 | Kim et al. | |
| 2013/0298268 A1 | 11/2013 | West | |
| 2013/0326645 A1 | 12/2013 | Cost et al. | |
| 2014/0041066 A1 | 2/2014 | Carlson et al. | |
| 2014/0120612 A1 | 5/2014 | Doyon et al. | |

FOREIGN PATENT DOCUMENTS

| | | |
|---|---|---|
| CN | 102559762 | 7/2012 |
| WO | 2000053779 | 9/2000 |
| WO | 2010079430 | 7/2010 |
| WO | 2011017315 | 2/2011 |
| WO | 2011019385 | 2/2011 |

(Continued)

OTHER PUBLICATIONS http://en.wikipedia.org/wiki/Livestock, accessed Aug. 8, 2014.*
http://waynesword.palomar.edu/trfeb98.htm, accessed Aug. 8, 2014.*
Molecular Biotechnology Ristevski et al. "Making better transgenic models." (2005);29(2):pp. 153-163.*
Sigmund et al."Viewpoint: Are Studies in Genetically Altered Mice Out of Control?" Arteriosclerosis, Thrombosis, and Vascular Biology.( 2000); 20:pp. 1425-1429.*
http://en.wikipedia.org/wiki/Vertebrate, acessed Aug. 8, 2014.*
Rogers et al. "Disruption of the CFTR Gene Produces a Model of Cystic Fibrosis in Newborn Pigs." Science. Sep. 26, 2008; 321(5897): 1837-1841.*

(Continued)

Primary Examiner — Titilayo Moloye
(74) Attorney, Agent, or Firm — Wilson Sonsini Goodrich & Rosati

(57) ABSTRACT

A genetically modified livestock animal comprising a genomic modification to an eIF4G gene. Cells, genes, and proteins encompassing a protease-resistant eIF4G protein or gene.

10 Claims, 2 Drawing Sheets
Specification includes a Sequence Listing.

(56) References Cited

FOREIGN PATENT DOCUMENTS

| WO | 2011054011 | 5/2011 |
|---|---|---|
| WO | 2011072246 | 6/2011 |
| WO | 2011154393 | 12/2011 |
| WO | 2012012738 | 1/2012 |
| WO | 2012152912 | 11/2012 |
| WO | 2012168304 | 12/2012 |
| WO | 2012168307 | 12/2012 |
| WO | 2013088446 | 6/2013 |
| WO | 2013191769 | 12/2013 |

OTHER PUBLICATIONS

Denning and Priddle. "New frontiers in gene targeting and cloning: success, application and challenges in domestic animals and human embryonic stem cells."Reproduction. Jul. 2003;126(1):1-11.*
Porteus and Carroll. "Gene targeting using zinc finger nucleases."Nat Biotechnol. Aug. 2005;23(8):967-73.*
Rogers et al. "Disruption of the CFTR gene produces a model of cystic fibrosis in newborn pigs."Science. Sep. 26, 2008;321(5897):1837-41.*
Belsham et al. "Foot-and-mouth disease virus 3C protease induces cleavage of translation initiation factors eIF4A and eIF4G within infected cells."J Virol. Jan. 2000;74(1):272-80.*
Whyte and Prather"Cell Biology Symposium: Zinc finger nucleases to create custom-designed modifications in the swine (Sus scrofa) genome."J Anim Sci. Apr. 2012;90(4):1111-7.*
Tian et al. "Cloning animals by somatic cell nuclear transfer—biological factors."Reprod Biol Endocrinol. 2003; 1: 98.*
Whitelaw and Sang. "Disease-resistant genetically modified animals."Rev Sci Tech. Apr. 2005;24(1):275-83.*
Carlson et al. "Targeting DNA With Fingers and TALENs."Mol Ther Nucleic Acids. Jan. 2012; 1(1): e3.*
Hochedlinger K. and Jaenisch R. "Nuclear reprogramming and pluripotency." Nature. Jun. 29, 2006;441(7097):1061-7.*
Kolata G. "Researchers Find Big Risk Defect in Cloning Animals."accessed from http://www.nytimes.com/2001/03/25/world/researchers-find-big-risk-of-defect-in-cloning-animals.html. Published Mar. 25, 2001.*
Ormandy et al. "Genetic engineering of animals: Ethical issues, including welfare concerns."Can Vet J. May 2011; 52(5): 544-550.*
Biase et al. "Massive dysregulation of genes involved in cell signaling and placental development in cloned cattle conceptus and maternal endometrium."Proc Natl Acad Sci U S A. Dec. 20, 2016;113(51):14492-14501.*
Aboussekkra et al., "Semidominant Suppressors of Srs2 Helicase Mutations of Saccharomyces cerevisiae Map in the RAD51 Gene, Whose Sequence Predicts a Protein with Similarities to Procaryotic RecA Proteins", Molecular and Cellular Biology, vol. 12(7):3224-3234 (Jul. 1992).
Aitken et al., "A Mechanistic Overview of Translation Initiation in Eukaryotes", Nature Structural & Molecular Biology, vol. 19(6):568-576 (Jun. 2012).
Basile et al., "Nucleotide Sequence and Transcriptional Regulation of the Yeast Recombinational Repair Gene RAD51", Molecular and Cellular Biology, vol. 12(7):3235-3246 (Jul. 1992).
Bedell et al., "In Vivo Genome Editing Using High Efficiency TALENs", Nature, vol. 491(7422):114-118 (Nov. 1, 2012).
Belsham et al., "Foot-and-Mouth Disease Virus 3C Protease Induces Cleavage of Translation Initiation Factors eIF4A and eIF4G Within Infected Cells", Journal of Virology, vol. 74(1):272-280 (Jan. 2000).
Borman et al., "eIF4G and its Proteolytic Cleavage Products: Effect on Initiation of Protein Synthesis From Capped, Uncapped, and IRES-Containing mRNAs", RNA, vol. 3:186-196 (1997).
Branda et al., "Talking about a Revolution: The Impact of Site-Specific Recombinases on Gentic Analyses in Mice", Developmental Cell, vol. 6:7-28, (Jan. 2004).

Coa et al., "Functional Analysis of the Two Alternative Translation Initiation Sites of Foot-and-Mouth Disease Virus" Journal of Virology, vol. 69(1):560-563 (Jan. 1995).
Carbery et al., "Targeted Genome Modification in Mice Using Zinc-Finger Nucleases", Genetics, vol. 186:451-459 (Oct. 2010).
Carlson et al., "Strategies for Selection Marker-Free Swine Transgenesis Using the Sleeping Beauty Transposon System." Transgenic Research, 13 pages (Jan. 9, 2011).
Carlson et al., "Efficient TALEN-Mediated Gene Knockout in Livestock" Proceedings of the National Academy of Sciences, 109(43):17382-17387 (Oct. 23, 2012).
Carlson et al., "Targeting DNA with Fingers and TALENs" Molecular Therapy-Nucleic Acids, 1-4 (Jan. 24, 2012).
Cermak et al., "Efficient Design and Assembly of Custom TALEN and Other TAL Effector-Based Constructs for DNA Targeting", Nucleic Acids Research, vol. 39(12):1-11 (Apr. 14, 2011).
Chinsangaram et al., "Protection of Swine by Live and Inactivated Vaccines Prepared From a Leader Proteinase-Deficient Serotype A12 Foot-and-Mouth Disease Virus", Vaccine, vol. 16(16):1516-1522 (Nov. 16, 1998).

Chinsangaram et al., "Inhibition of L-Deleted Foot-and-Mouth Disease Virus Replication by Alpha/Beta Interferon Involves Double-Stranded RNA-Dependent Protein Kinase", Journal of Virology, vol. 75(12):5498-5503 (Mar. 20, 2001).

Christian et al., "Targeting DNA Double-Strand Breaks with TAL Effector Nucleases", Genetics, vol. 186:757-761 (Oct. 2010).

Cibelli et al., "Cloned Transgenic Calves Produced From Nonquiescent Fetal Fibroclasts", Science vol. 280:1256-1258 (May 22, 1998).

Clark et al., "Enzymatic Engineering of the Porcine Genome with Transposons and Recombinases", BMC Biotechnology, vol. 7(42):1-17 (Jul. 17, 2007).

Cong et al., "Multiplex Genome Engineering Using CRISPR/Cas Systems", Science Express, 7 Pages (Jan. 3, 2013).

Cui et al., "RecA-Mediated, Targeted Mutagenesis in Zebrafish", Marine Biotechnology, vol. 5:174-184 (2003).

De Los Santos et al., "The Leader Proteinase of Foot-and-Mouth Disease Virus Inhibits the Induction of Beta Interferon mRNA and Blocks the Host Innate Immune Response", Journal of Virology, vol. 80(4):1906-1914 (Feb. 2006).

De Los Santos et al., "Degradation of Nuclear Factor Kappa B During Foot-and-Mouth Disease Virus Infection" Journal of Virology, vol. 81(23):12803-12815 (Dec. 2007).

De Los Sanitos et al., "A Conserved Domain in the Leader Proteinase of Foot-and-Mouth Disease Virus Is Required for Proper Subcellular Localization and Function", Journal of Virology, vol. 83(4):1800-1810 (Feb. 2009).

Dicarlo et al., "Genome Engineering in *Saccharomyces cerevisiae* Using CRISPR-Cas Systems", Nucleic Acids Research Advance Access, 8 pages (2013).

Drake et al., "Mutation Rates Among RNA Viruses", Proceedings of the National Academy of Sciences, vol. 96 (24):13910-13913 (Nov. 23, 1999).

Dupuy et al., "Mammalian Germ-Line Transgenesis by Transposition", Proc Natl Acad Sci, vol. 99(7):4495-4499 (Apr. 2, 2002).

Fabian et al., "The Mechanics of miRNA-Mediated Gene Silencing: A Look Under the Hood of miRISC", Nature Structural & Molecular Biology, vol. 19(6):586-593 (Jun. 2012).

Foeger et al., "The Binding of Foot-and-Mouth Disease Virus Leader Proteinase to elF4GI Involves Conserved Ionic Interactions", FEBS Journal, vol. 272:2602-2611 (2005).

Freistadt et al., "Biochemical Characterization of the Fidelity of Poliovirus RNA-Dependent RNA Polymerase", Virology Journal, 4(44): 11 pages (May 24, 2007).

Geurts et al., "Knockout Rats Produced Using Designed Zinc-Finger Nucleases", Science, vol. 325(5939) 3 Pages (Jul. 24, 2009).

Glaser et al., "Extremely Efficient Cleavage of elF4G by Picornaviral Proteinases L and 2A in Vitro" FEBS Letters, vol. 480:151-155 (2000).

Gradi et al., "Cleavage of Eukaryotic Translation Initiation Factor 4GII Within Foot-and-Mouth Disease Virus-Infected Cells:Identification of the L-Protease Cleavage Site in Vitro" Journal of Virology, vol. 78(7):3271-3278 (Apr. 2004).

(56) References Cited

OTHER PUBLICATIONS

Grobet et al., "A Deletion in the Bovine Myostatin Gene Causes the Double-Muscled Phenotype in Cattle", Nature Genetics, vol. 17:71-74 (Sep. 17, 1997).
Grubman et al., "Foot-and-mouth Disease", Clinical Microbiology Reviews, vol. 17(2):465-493 (Apr. 2004).
Guatelli et al., "Isothermal, In Vitro Amplification of Nucleic Acids by a Multienzyme Reaction Modeled After Retroviral Replication", Proc. Natl. Acad. Sci., vol. 87:1874-1878 (Mar. 1990).
Guschin et al., "A Rapid and General Assay for Monitoring Endogenous Gene Modification." Methods in Molecular Biology, 649:247-256, (2010).
Hinton et al., "Conservation of L and 3C Proteinase Activities Across Distantly Related Aphthoviruses", Journal ofGeneral Virology, vol. 83:3111-3121 (2002).
Hinton et al., "Functional Analysis of Individual Binding Activities of the Scaffold Protein elF4G" Journal Biological Chemistry, vol. 282(3):1695-1708 (Jan. 19, 2007).
Hyrup et al., "Peptide Nucleic Acids (PNA): Synthesis, Properties and Potential Applications", Bioorganic & Medicinal Chemistry, vol. 4(1):5-23 (1996).
Kambadur et al., "Mutations in myostatin (GDF8) in Double-Muscled Belgian Blue and Piedmontese Cattle", Genome Research, vol. 7:910-915 (1997).
Kawakami, "To12: A Versatile Gene Transfer Vector in Vertebrates", Genome Biology, vol. 8(1):S7.1-S7.10 (2007).
Kerekatte et al., "Cleavage of Poly(A)-Binding Protein by Coxsackievirus 2A Protease in Vitro and in Vivo: Another Mechanism for Host Protein Synthesis Shutoff?" Journal of Virology, 73(1):709-717 (Sep. 25, 1998).
Kiwaki et al., "Correction of Ornithine Transcarbamylase Deficiency in Adult spfash Mice and in OTC-Deficient Human Hepatocytes with Recombinant Adenoviruses Bearing the CAG Promoter", Human Gene Therapy, vol. 7:821-830 (May 1, 1996).
Lamphear et al., "A Single Amino Acid Change in Protein Synthesis Initiation Factor 4G Renders Cap-Dependent Translation Resistant to Picornaviral 2A Proteases" Biochemistry, 35:15726-15733 (1996).
Lavitrano et al., "Efficient Production by Sperm-Mediated Gene Transfer of Human Decay Accelerating Factor (hDAF) Transgenic Pigs for Xenotransplantation", Proc. Natl. Acad. Sci., vol. 99:(22):14230-14235 (Oct. 29, 2002).
Lavitrano et al., "Sperm-Mediated Gene Transfer", Reproduction, Fertility and Development, vol. 18:19-23 (2006).
Lee et al., "Attenuated Vaccines Can Recombine to Form Virulent Field Viruses" Science, vol. 337:188 (Jul. 13, 2012).
Lloyd, "Translational Control by Viral Proteinases" Virus Research, 119:76-88 (2006).
Lo, "Transformation by Iontophoretic Microinjection of DNA: Multiple Integrations Without Tandem Insertions", Molecular and Cellular Biology, vol. 3(10):1803-1814 (Oct. 1983).
Lopez De Quinto et al., "Interaction of the elF4G Initiation Factor with the Aphthovirus IRES is Essential for Internal Translation Initiation in Vivo", RNA, vol. 6:1380-1392 (2000).
Ma et al., "High Efficiency In Vivo Genome Engineering with a Simplified 15-RVD GoldyTALEN Design", PLOS One, vol. 8(5):1-8 (May 29, 2013).
Maeshima et al., "RAD51 Homologues in Xenopus Laevis: Two Distinct Genes are Highly Expressed in Ovary and Testis", Gene 160:195-200 (1995).
Mali et al., "RNA-Guided Human Genome Engineering via Cas9", Science, vol. 339:823-826 (Feb. 15, 2013).
Mason et al., "Evaluation of a Live-Attenuated Foot-and-Mouth Disease Virus as a Vaccine Candidate", Virology, vol. 227:96-102 (1997).
Miller et al., "A TALE Nuclease Architecture for Efficient Genome Editing", Nature Biotechnology, vol. 29(2):143-(2011) Nature Biotechnol 29:143 (Feb. 2011).
Miskey et al., "The Frog Prince: A Reconstructed Transposon from Rana Pipiens with High Transpositional Activity in Vertebrate Cells", Nucleic Acids Research, vol. 31(23):6873-6881 (Oct. 15, 2003).
Miskey et al., "The Ancient Mariner Sails Again: Transposition of the Human Hsmar1 Element by a Reconstructed Transposase and Activities of the SETMAR Protein of Transposon Ends", Molecular and Cellular Bioligy, vol. 27 (12):4589-4600 (Jun. 2007).
Morita et al., "A Mouse Homolog of the *Escherichia coli* recA and *Saccharomyces cerevisiae* RAD51 Genes" Proc. Natl. Acad. Sci. vol. 90:6577-6580 (Jul. 1993).
Mussolino et al., "A Novel TALE Nuclease Scaffold Enables High Genome Editing Activity in Combination With Low Toxicity", Nucleic Acids Research, vol. 39(21):9283-9293 (Jul. 5, 2011).
Orban et al.., "Tissue-and Site-Specific DNA Recombination in Transgenic Mice", Proc. Natl. Acad. Sci. vol. 89:6861-6865 (Aug. 1992).
Pavlopoulos et al., "The DNA Transposon Minos as a Tool for Transgenesis and Functional Genomic Analysis in Vertebrates and Invertebrates", Genome Biology vol. 8(Suppl.1):S2.1-S2.7 (Oct. 31, 2007).
Perez-Martin et al., "Bovine Type III Interferon Significantly Delays and Reduces the Severity of Foot-and-Mouth Disease in Cattle" Journal of Virology, vol. 86:4477-4487 (Jan. 23, 2012).
Pfeiffer et al., "Increased Fidelity Reduces Poliovirus Fitness and Virulence Under Selective Pressure in Mice" PLoS Pathogens, vol. 1(2):0102-0110 (Oct. 2005).
Piccone et al., "The Foot-and-Mouth Disease Virus Leader Proteinase Gene is not Required for Viral Replication", Journal of Virology, vol. 69(9):5372-5382 (May 26, 1995).
Prevot et al., "Conducting the Initiation of Protein Synthesis: The Role of Eif4g", Biology of the Cell, vol. 95:141-156 (Mar. 4, 2003).
Roberts et al., "Recognition of Picornavirus Internal Ribosome Entry Sites Within Cells; Influence of Cellular and Viral Proteins", RNA, vol. 4:520-529 (1998).
Saleh et al., "Functional Interaction of Translation Initiation Factor elF4G with the Foot-and-Mouth Disease Virus Internal Ribosome Entry Site", Journal General Virology, vol. 82:757-763 (2001).
Santos et al., "Hydrolytic Properties and Substrate Specificity of the Foot-and-Mouth Disease Leader Protease", Biochemistry, vol. 48:7948-7958 (2009).
Shinohara et al., "Closing of Human, Mouse and Fission Yeast Recombination Genes Homologous to RAD51 and recA", Nature Genetics, vol. 4:239-243 (Jul. 1993).
Strong et al., "Sequential Modification of Translation Initiation Factor elF4GI by Two Different Foot-and-Mouth Disease Virus Proteases Within Infected Baby Hamster Kidney Cells: Identification of the 3Cpro Cleavage Site" Journal of General Virology, vol. 85:2953-2962 (2004).
Summerton et al., Morpholino Antisense Oligomers: Design, Preparation, and Properties, Antisense & Nucleic Acid Drug Development vol. 7:187-195 (1997).
Tan et al., "Precision Editing of Large Animal Genomes", Advances in Genetics, vol. 80:37-97 (2012).
Tesson et al., "Knockout Rats Generated by Embryo Microinjection of TALENs", Nature Biotechnology, vol. 29 (8):695-696 (Aug. 2011).
Truniger et al., "Recessive Resistance to Plant Viruses", Advances in Virus Research, vol. 75:120-159 (2009).
Thompson et al.,"Germ Line Transmission and Expression of a Corrected HPRT Gene Produced by Gene Targeting in Embryonic Stem Cells", Cell, vol. 56:313-321 (Jan. 27, 1989).
Thompson et al., "Economic Costs of the Foot and Mouth Disease Outbreak in the United Kingdom in 2001", Rev. Sci. Tech., vol. 21(3):657-687 (2002).
Van Der Putten et al., "Efficient Insertion of Genes into the Mouse Germ Line via Retroviral Vectors", Proc. Natl. Acad. Sci., vol. 82:6148-6152 (Sep. 1985).
Visscher et al., "Breeding Objectives for Pasture Based Dairy Production Systems", Livestock Production Science, vol. 40:123-137(Feb. 1, 1994).

(56) References Cited

OTHER PUBLICATIONS

Wakayama et al., "Full-Term Development of Mice From Enucleated Oocytes Injected with Cumulus Cell Nuclei", Nature vol. 394:369-374 (Jul. 23, 1998).
Wang et al., The Leader Proteinase of Foot-and-Mouth Disease Virus Negatively Regulates the Interferon Pathway by Acting as a Viral Deubiquitinase. Journal of Virology, vol. 85(8):3758-3766 (Feb. 9, 2011).
Wang et al., "Foot-and-Mouth Disease Virus Leader Proteinase Inhibits dsRNA-induced Type I Interferon Transcription by Decreasing Interferon Regulatory Factor 3/7 in Protein Levels", Biochemical and Biophysical Research Communications, vol. 399:72-78 (2010).
Weiss, "Hot Prospect for New Gene Amplifier", Science, vol. 254:1292-1293 (Nov. 1991).
Wilmut et al., "Viable Offspring Derived from Fetal and Adult Mammalian Cells", Nature vol. 385:810-813 (Feb. 1997).
Xu et al., "CMV-β-Actin Promoter Directs Higher Expression From an Adeno-Associated Viral Vector in the Liver than the Cytomegalovirus or Elongation Factor 1α Promoter and Results in Therapeutic Levels of Human Factor X in Mice", Human Gene Therapy, vol. 12:563-573 (Mar. 20, 2001).
Zhao et al., "Protection of Cap-Dependent Protein Synthesis in Vivo and in Vitro with an eIF4G-1 Variant Highly Resistant to Cleavage by Coxsackievirus 2A Protease", Journal of Biological Chemistry, vol. 278(7):4449-4457 (2003).
International Search Report and Written Opinion from corresponding PCT Application No. PCT/US2013/051222, 17 pages, dated Oct. 16, 2013.
Carlson et al., "Adding and Subtracting Livestock Genes With Transposons and Nucleases", Transgenic Res, vol. 21(4):901-902 (Aug. 2012).
Carlson et al., "Editing Livestock Genomes With Site-Specific Nucleases", Reproduction, Fertility and Development, vol. 26:74-82 (2014).
Doyon et al., "Heritable Targeted Gene Disruption in Zebrafish Using Designed Zinc Finger Nucleases", Nature Biotechnology, vol. 26(6):702-708 (Jun. 2008).
Fahrenkrug et al., "95 Production of Gene-Edited Pigs, Cattle, and Lambs by Embryo Injection of TALENS or ZFNs", Reproduction, Fertility and Development, vol. 26(1):161 (Dec. 5, 2013). Absrtact Only.
Hauschild et al., "Efficient Generation of a Biallelic Knockout in Pigs Using Zinc-Fingers Nucleases", Proceedings of the National Academy of Sciences, vol. 108(29):12013-12017 (Jul. 19, 2011).
Huang et al., "Heritable Gene Targeting in Zebrafish Using Customized TALENs", Nature Biotechnology, vol. 29 (8):699-700 (Aug. 2011).
Jinek et al., "RNA-Programmed Genome Editing in Human Cells", eLife 9 Pages (2013).
Lillico et al., "Live Pigs Produced From Genome Edited Zygotes", Scientific Reports, 4 pages (Oct. 10, 2013).
Proudfoot et al., "Genome Edited Sheep and Cattle", Transgenic Research, vol. 24:147-153 (Sep. 10, 2014).
Santos et al., "Foot and Mouth Disease Leader Protease (Lbpro): Investigation of Prime Side Specificity Allows the Synthesis of a Potent Inhibitor", Biochimie, vol. 94:711-718 (2012).
Whitelaw et al., "Disease-Resistant Genetically Modified Animals", Scientific and Technical Review of the Office International des Epizooties, vol. 24(1):275-283 (2005).
Database WPI, Thomson Scientific, London, GB: XP002754106 (Jul. 11, 2012). Abstract.
Supplementary European Search Report from Corresponding European Application No. 13825988.2, 12 Pages, dated Feb. 29, 2016.
Castello et al., "The Multifaceted Poliovirus 2A Protease: Regulation of Gene Expression by Picornavirus Proteases", Journal of Biomedicine and Biotechnology, vol. 2011, 23 Pages (Feb. 17, 2011).

* cited by examiner

PRODUCTION OF FMDV-RESISTANT LIVESTOCK BY ALLELE SUBSTITUTION

CROSS REFERENCE TO RELATED APPLICATIONS

This patent application claims priority to U.S. Provisional No. 61/677,904 filed Jul. 31, 2012, which is hereby incorporated by reference herein.

TECHNICAL FIELD

The technical field relates to genetically modified animals and associated techniques.

BACKGROUND

Cloven-hoofed animals infected by Foot and Mouth Disease Virus (FMDV) become rapidly incapacitated by acute vesicular disease. FMD infection of cattle and pigs causes fever, painful blistering, lameness and loss of appetite. As suggested by the name of the infectious agent, secondary infections of the feet often occur, causing chronic lameness and delayed healing and similarly mastitis may be a common sequel in dairy cattle. The acute phase of the disease lasts for approximately a week receding in the face of a mounting immune response of which the antibody response appears to be of particular importance as it is highly efficient in clearing virus from the blood stream. Mortality can occur in young animals due to infection of the heart muscle causing circulatory failure. The disease is so highly contagious that infection in a single animal calls for the destruction and burial of the entire herd. Hence FMDV is considered by some to be the world's most important pathogen of domesticated farm animals. In 2001 an FMD outbreak in Great Britain resulted in total losses of about $12-4 billion [1] and more than a decade ago, the University of California Davis estimated that an FMD outbreak just in California could cost from $6-14 billion in control costs and lost markets due to restrictions in movement and sales of animals. Sales of milk and other products, as well as meat, would be halted and jobs of producers and workers in related industries would be lost or severely curtailed. The economic effects in other countries are proportional.

SUMMARY OF THE INVENTION

Animals that are resistant to FMDV are described herein. The animals may be made with only a minimal nucleotide change and with the change being made at an exact location without making other changes to the animals' genome.

An embodiment of the invention is a genetically modified animal comprising a genomic modification to an eIF4G gene. The modification may comprise, for example an insertion, a deletion, or a substitution of one or more bases of an eIF4G gene. The eIF4G gene may be altered so that it is expressing an eIF4G protein altered relative to a wild type eIF4G protein of the animal to be resistant to cleavage by a proteinase of a foot-and-mouth disease virus enzyme, e.g., one or both of a leader proteinase of foot-and-mouth disease virus enzyme (Lpro) and a virus encoded 3C protease of foot-and-mouth disease virus enzyme (3Cpro). The animal may be a mammal. The animal may be a laboratory research animal (e.g., mouse, rat, dog or species of pig used in laboratories, e.g., miniature swine). The animal may be a livestock animal, e.g., selected from a group consisting of pig, fish, rabbit, cow, chicken, goat, and sheep. In some case, the animal is from a first breed and the genomic modification is a natural allele of the eIF4G gene found in another breed of the animal. In another case, the animal is from a first species and the genomic modification is an allele of the eIF4G gene in another breed of a second species (human or non-human animal). The allele is, in general, not an entire gene, but is a portion of a gene that codes for a protein portion that mediates binding and proteolysis by a FMDV protease. The animal may be homozygous or heterozygous for the modified eIF4G gene. The animal may be a founder animal or a progeny of a founder animal, i.e., a new breed or line of animals may be created. The animal may be comprising the eIF4G protein expressed by the modified eIF4G gene. The animal may be resistant to foot and mouth disease. The modified eIF4G protein may be modified to prevent binding of one of, or both of, Lpro and Cpro.

An embodiment of the invention is a method of creating a genetically modified organism comprising altering a native eIF4G gene of a primary cell or an embryo in vitro (or in the womb in the case of an embryo) and cloning the primary cell or implanting the embryo into a mother animal (surrogate), with the eIF4G gene being altered to express an eIF4G isoform that resists proteolysis by a foot and mouth disease protease. The method can involve transfecting the primary cell or the embryo with a site-specific nuclease that specifically cleaves a site in the native eIF4G gene, and a nucleic acid template that comprises at least a portion of the eIF4G gene, with the template providing an alternative allele for the native eIF4G gene, said alternative allele encoding an eIF4G isoform that is resistant to cleavage by a proteinase of a foot-and-mouth disease virus enzyme. An example of a site-specific nuclease is a nuclease-based system chosen from the group consisting of a zinc finger nucleases (ZFN), transcriptional activator-like effector nucleases (TALEN) and a Clustered Regularly Interspaced Short Palindromic Repeat (CRISPR or sometimes referred to as CRISPR/Cas9).

An embodiment is an in vitro cell comprising a genomic modification to an eIF4G gene. The eIF4G gene may be expressing an eIF4G protein altered relative to a wild type eIF4G protein of the animal to be resistant to cleavage by a proteinase of a foot-and-mouth disease virus enzyme. The cell may be selected from a group consisting of mouse, rat, horse, mini-pig, pig, fish, rabbit, cow, chicken, goat, artiodactyl, ungulate, and sheep. The cell may further comprising the eIF4G protein expressed by the modified eIF4G gene.

Embodiments of the invention include an isolated nucleic acid encoding an isoform of any of the eIF4G proteins, such as an eIF4G protein that is resistant to cleavage by a proteinase of a foot-and-mouth disease virus enzyme.

Embodiments of the invention include cells, organisms, or animals that include an exogenous gene that expresses an EIF4G protein or a portion of said protein that is bound by an FMDV protease. The exogenous gene expression competes for FMDV virus binding so that native protein cleavage is reduced. Alternatively, the exogenous gene expression of a protease-resisting EIF4G provides continued cellular function with the cell is infected. An embodiment is a method of creating a genetically modified organism comprising adding expression of an exogenous eIF4G gene to a primary cell or an embryo in vitro and cloning the primary cell or implanting the embryo into a mother animal, with the exogenous eIF4G gene expressing an eIF4G isoform that resists proteolysis by a foot and mouth disease protease. An embodiment is an in vitro cell comprising a genomic modification to an eIF4G gene or a nucleic acid that expresses an exogenous eIF4G gene.

DETAILED DESCRIPTION

This disclosure explains how to make animals that are resistant to FMDV. The animals are genetically modified so that their eukaryotic translation initiation factor 4G proteins (eIF4G) are resistant to cleavage by one or both of the FMDV proteases $L^{pro}$ and $3C^{pro}$ (collectively referred to herein as the FMDV proteases). These are proteases made by FMDV that attack eIF4G proteins. The working examples include the generation of a livestock primary cell modified to resist attack by one of the FMDV proteases. Animals can be cloned from these cells using techniques proven by the inventors to be effective to make founder animals. The modification may be made in a site-specific manner so that the native gene allele is modified to make a modified allele that expresses FMDV protease-resistant eIF4G proteins.

FMDV Resistance

FMDV belongs to the *Aphthovirus* genus of the picornaviridae family, the smallest of animal viruses that include poliovirus, rhinovirus (common cold), and hepatitis A. There are seven serotypes with multiple subtypes [2]. Like other picornaviruses, the FMDV genome is a single-stranded RNA of about 8,500 nucleotides that can be directly translated (positive-strand genome) that encodes a single polyprotein in excess of 100 KDa. Encoded in the N-terminal region of the FMDV RNA is a papain-like protease, called $L^{pro}$ that has two isoforms, Lab and Lb of which Lb is the important product [3]. $L^{pro}$ is both exceptionally small and exceptionally specific. The $L^{pro}$ sequence first cleaves the FMDV polyprotein, while it is being synthesized, to liberate itself from the polyprotein. Then the free $L^{pro}$ further cuts the remaining polyprotein into individual functional polypeptides that produce massive numbers of progeny virus. $L^{pro}$ has several other target sites of which the most important appears to be eukaryotic translation initiation factor 4G (eIF4G) [4, 5] that when cleaved by $L^{pro}$ is unable to promote initiation of the $^{4m}$G-capped mRNAs of mammalian cells. EIF4G, which comes in two isoforms eIF4GI and eIF4GII, is a scaffold protein that brings together several eIF4 RNA-binding proteins that attach to structures at the 5' and 3' ends of all capped and polyadenylated mRNAs. In some picornaviruses, e.g., poliovirus, the $2A^{pro}$ protease has the equivalent activities as $L^{pro}$.

Figure 1:
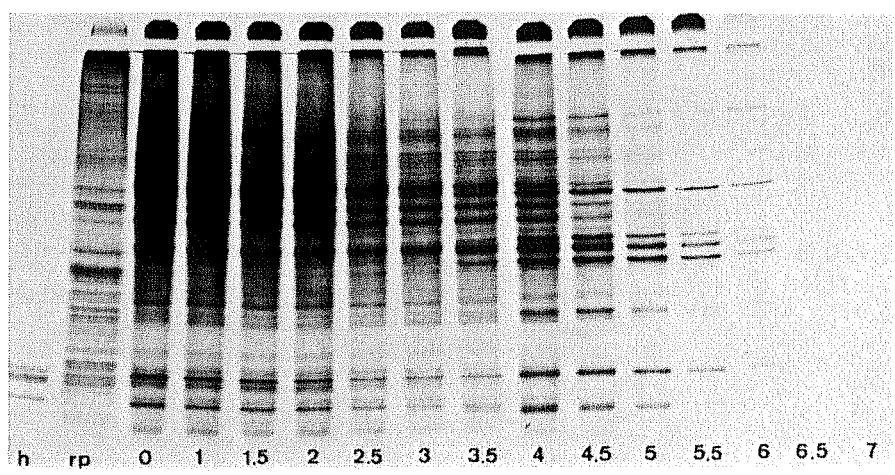
FIG. 1 is a radioautography of electrophoresis profiles of total cellular protein in vivo; the $^{35}$S-labeled total proteins from cells are imaged as a function of time post-picornaviral infection in hours at the bottom; complete cell lysis (after 6.5 hr) shows the time course for shutoff of host proteins and the near total takeover of polypeptide synthesis by picornaviral proteins. The prominent bands at 5 hr are viral proteins cleaved by $L^{pro}$ from the polyprotein precursor (heavy band at the top of the gel). The strong bands near the bottom of the gel are histones that derive from non-polyadenylated mRNA and thus not eIF4G-dependent and sensitive to viral proteinase activity.

The net effect of eIF4G is to non-covalently bridge the termini eukaryotic mRNAs that have $^{7mG}$cap-binding eIF4E bound to their 5'-ends and poly(A)-binding protein (PABP) at their 3'-ends [6, 7]. These additions to the termini of mRNAs allow the translational machinery to differentiate completely processed mRNAs from the myriad of other RNA molecules in a cell to coordinate their translation into proteins. The critical activity of eIF4G proteins makes them attractive targets for cleavage by viral invaders that have evolved to subjugate the translational machinery of the cell to produce exclusively viral proteins [8-12]. Once cut into two or more peptides, eIF4G is incapable of bridging the 5' and 3' ends of mRNAs, and host protein synthesis come to a halt over a few hours (FIG. 1). The proteases have side activities that target proteins such as interferons and its regulators [13-16] as well as nuclear factor kappa B [17] that are involved with immune responses to viruses, especially viruses that have a double-stranded RNA intermediate (or final) product over the course of their replication. Interaction of cleaved eIF4G peptides with the FMDV internal ribosome initiation site appears to be important for expression of FMDV genes [18-21].

Picornaviral genomes are not capped and hence do not require the assistance of eIF4G to initiate translation of their encoded polyproteins. Rather, initiation of translation of the polyprotein precursor occurs at internal ribosome entry site (IRES). As a result, nearly all synthesis of host-cell proteins is shutoff leaving the protein synthetic machinery almost exclusively available for the production of viral proteins. This feature is the key to the rapid spread and onset of symptoms in virally infected animals. There is a second protease, $3C^{pro}$ that also attacks eIF4G, PABP and the RNA helicase eIF4A [22]. However, the activity of $3C^{pro}$ is delayed and generally has a lesser role than $L^{pro}$ in subversion of host protein synthesis [11, 23, 24]. These two features of $L^{pro}$ and $3C^{pro}$ are essential to virus debilitation and spread. Although one study using cultured BHK-21 cells showed that FMDV lacking to $U^{pro}$ replicated at a slightly lower rate [25], FMDV lacking to $U^{pro}$ was markedly non-virulent when injected into cattle and pigs and was unable to spread to co-housed animals [26, 27]. The $U^{pro}$-deficient virus was susceptible to interferon-mediated cell defenses in the whole animal but not in the cultured cells [27, 28].

The effective strategy of picornaviruses is therefore: inactivate host protein synthesis by attacking its weakest point, the bridging function of eIF4G, using the same viral proteases that are necessary for polyprotein cleavage into mature proteins. As this is done, the viral genome replicates via a double-stranded intermediate that will not induce significant intra-cellular immune responses because 1) synthesis of the necessary host proteins is compromised and 2)

several host defense proteins have amino acid sequences that are targeted by the viral proteases. The virus is cytocidal due to subversion of normal cellular activities; infectious virions appear 4-6 hours post-infection.

An embodiment of the invention is an animal with an eIF4G gene encoding an eIF4G protein that resists proteases made by FMDV. One FMDV resistant embodiment is to make only one or only a few nucleotide-specific changes in the eIF4G genes that will confer an eIF4G protein with resistance to $C^{pro}$ and/or to $L^{pro}$. Such precision genetic changes to an animal genome may be made with site-specific nucleases such as zinc finger nucleases (ZFNs), transcriptional activator-like effector nucleases (TALENs), or Clustered Regularly Interspaced Short Palindromic Repeats (CRISPRs). TALENs are a more versatile platform than ZFNs [34, 35]. CRISPR is a recent and effective tool (Cong et al., Science express, Jan. 3, 2013 ¶. 1-7; Mali et al., Science 15 Feb. 2013: Vol. 339, pp. 823-826). Example 2 describes primary cells that have been genomically modified to make its EIF4G into an FMDV-protease resistant gene. These cells may be used to make cloned animals using conventional techniques.

One embodiment of the animal has the resistant gene in the genome of the animal. An alternative embodiment adds an exogenous gene to the animal, which expresses the exogenous gene in some or all cells. The exogenous gene resists FMDV activity. Embodiments of the invention include cells, organisms, or animals that include an exogenous gene that expresses an EIF4G protein or a portion of said protein that is bound by an FMDV protease. Another alternative embodiment places the eIF4G gene under control of an inducible promoter. In use, for instance, a group of animals can receive an additive in their feed or otherwise to activate the gene to create resistance. Founder animals and breeds may be established with one or more of these features.

By substituting specific amino acids in the eIF4GI and eIF4GII sequences that retain translational function but are resistant to protease digestion, host protein synthesis can continue to outcompete synthesis of viral proteins due to the massive excess of host mRNAs, which are not degraded in picornavirus-infected cells [36]. Moreover, IRES-mediated translation of FMDV RNA may be attenuated due to lack of eIF4G cleavage products [20, 21]. This approach provides resistance to FMDV replication and is better than merely adding protease-resistant eIF4G genes into genomes with protease-susceptible eIF4G genes [19, 36]. This strategy does not involve transgenesis; rather it is equivalent to gene conversion, a standard genetic activity in animal cells.

TABLE 1

Porcine, bovine and ovine eIF4G sequence and FMDV resistant isoforms

| Version | Sequence | |
|---|---|---|
| Wildtype | PSFANLGRPALS | SEQ ID NO: 1 |
| Isoform 1 | PSFADFGRPALS | SEQ ID NO: 2 |
| Isoform 2 | PSFANLGPPALS | SEQ ID NO: 3 |
| Isoform 3 | PSFANFGRPALS | SEQ ID NO: 4 |
| Isoform 4 | PSFANDGRPALS | SEQ ID NO: 5 |
| Isoform 5 | PSFANPGRPALS | SEQ ID NO: 6 |

TABLE 1-continued

Porcine, bovine and ovine eIF4G sequence and FMDV resistant isoforms

| Version | Sequence | |
|---|---|---|
| Isoform 6 | PSFANYGRPALS | SEQ ID NO: 7 |
| Isoform 7 | PSFANWGRPALS | SEQ ID NO: 8 |
| Isoform 8 | PSFADLGRPALS | SEQ ID NO: 9 |
| Isoform 9 | PSFPNLGRPALS | SEQ ID NO: 10 |
| Isoform 10 | PSFDNLGRPALS | SEQ ID NO: 11 |

Figure 2:
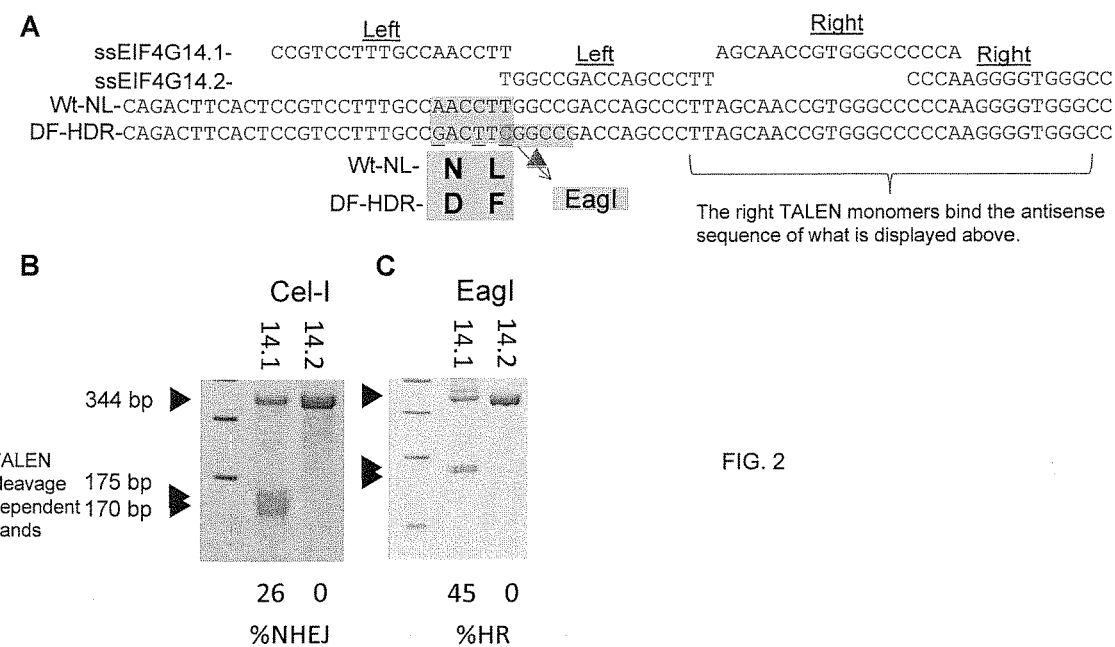
FIG. 2 shows experimental results for altering a portion of a EIF4GI gene. A sequence for a portion of a porcine EIF4GI is shown in panel A. The wild type sequence has asparagine and leucine residues in the minus 3 and 2 positions relative to the Lpro cleavage site (arrowhead). In this example, the a template is provided to guide replacement of the minus 3 and 2 residues with aspartic acid and phenylalanine so as to render the modified EIF4GI resistant to $L^{pro}$ cleavage. Two pairs of TALENs (top) were designed to cut the wild type EIF4GI to stimulate homologous recombination. Panel B) depicts results of a Surveyor (Cel-I) assay of pig fibroblasts transfected with each TALEN pair. Panel C) depicts RFLP assay to determine the efficiency of homologous recombination. The Figure includes left TALEN CCGTCCTTTGC-CAACCTT (SEQ ID NO:12), right TALEN AGCAAC-CGTGGGCCCCCA (SEQ ID NO:13); left TALEN TGGCCGACCAGCCCTT (SEQ ID NO:14); right TALEN CCCAAGGGGTGGGCC (SEQ ID NO:15); EIF4GI gene portion CAGACTTCACTCCGTCCTTTGCCAACCTTG-GCCGACCAGCCCTTAGCAACCGTGGGC CCCCAAGGGGTGGGCC (SEQ ID NO:16); and HDR CAGACTTCACTCCGTCCTTTGCCGACTTCGGC-CGACCAGCCCTTAGCAACCGTGGGC CCCCAAGGGGTGGGCC (SEQ ID NO:17).

By way of example, Table 1 shows the amino acid sequence form 668-679 for the portion of a porcine eIF4G gene (100% identity to bovine and ovine) that is bound by $L^{pro}$ and is cleaved by $L^{pro}$. Table 1 further shows alterations of one or two amino acids that are expected to cause resistance to degradation and create FMDV resistance, with the alterations being emphasized by underlining. The alternative amino acid sequences are isoforms of the eIF4G protein; the genes that encode the various isoforms are alleles of each other. Amino acids 668-679 are of wild type (Wt) porcine EIF4GI as translated from NM_001246253. Alternative isoforms to confer resistance to the FMDV $L^{pro}$ protease are predicted from (see Santos et al 2009 describing viral polypeptide sites; Biochemistry 48, 7948). Isoform 1 is based on alignment with human EIF4GII at this site. The human EIF4GII is not cleaved here and is functional. Isoforms 2 and 8 are similarly based on alignment with human EIF4GII. The remaining isoforms are accordingly chosen based on their likelihood to inhibit the proteases and maintain normal function. Artisans can easily create nucleic acid sequences to make the indicated isoforms and the wild type gene sequence is readily and publicly available. Homologous recombination (HR) templates may be generated to code the various isoforms along with silent RFLP mutations to aid in colony screening. These templates will have 90-mer oligonucleotides spanning the EIF4G14.1 TALEN binding sites (FIG. 2). Each HR template (typically from about 0.025 to about 0.8 nMole) along with EIF4G14.1 TALENs (typically from about 0.1 to about 10 micrograms) will be introduced into early passage fibroblasts, and individual colonies will be screened for introgression of the mutant alleles. Cells will be taken from colonies that incorporate the desired allele and used to clone founder animals.

Table 2 shows sources for sequences of various eIF4G genes in various livestock species. Artisans can readily obtain information for these and other livestock eIF4G genes.

TABLE 2

EIF4G orthologs and homologs in livestock

| | Gene | Ensembl ID | NCBI ID (mRNA) |
|---|---|---|---|
| Pig | EIF4GI | ENSSSCG00000030255 | |
| | EIF4G3* | ENSSSCG00000003512 | |
| | Novel uncharacterized | ENSSSCG00000026340 | |
| Cow | EIF4GI | ENSBTAG00000012881 | |
| | EIF4G3* | ENSBTAG00000040215 | |
| Sheep | EIF4GI | | XM_004003088.1 |

*Note that the EIF4G3 gene encodes the EiF4GII protein.

Accordingly, embodiments of the invention include an EIF4G that is resistant to an FMDV proteinase, e.g., $L^{pro}$ and/or $C^{pro}$. Embodiments include isoforms having changes to one or more residues (amino acid or nucleic acid) of the wild type, and also nucleic acid sequences encoding the same. The one or more altered residues may be in a position wherein an FMDV proteinase binds, or in a nucleic acid sequence corresponding to the same. Alternatively, the mutation may be at the point where the proteinase makes its cut in the protein. The number of changes relative to a wild type typically would encompasses from 1 to about 50 changes; artisans will immediately understand that all ranges and values between 1 and 50 are contemplated, e.g., from 1 to 5, from 1 to 10, and so forth. The changes are such that the EIF4G is operable to carry out normal (meaning non-FMDV) functions. Animals with the improved EIF4G animal will be resistant to foot and mouth disease. One form of resistance is immunity, meaning that the animal is essentially not affected by the disease. Another form or resistance is that the animal recovers more readily once it is infected. Another form of resistance is that the animal is harder to infect in the first place—as a result of the virus having difficulty spreading. A consequence of resistance can include a decreased likelihood of spreading the disease because viral titers in the host are greatly decreased.

Embodiments also include the genes, the proteins, the nucleic acids encoding the proteins, and the cells or animals with such genes and proteins. The animals are useful as livestock and as research animals to study FMDV. The cells are useful for making animals as livestock or as research animals and are also of use for FMDV research. Cells that resist FMDV proteolysis are useful for testing drugs and treatments that interfere with other aspects of the FMDV lifecycle. One reason is that the animals and cell will persist longer so that the effects of these other interventions can be assayed. Another reason is that the results of studies with other therapies can quickly determine if their mode of action is FMDV proteolysis, or not. The genes and the proteins, by themselves, are of further use for assaying FMDV testing and effects.

Genetically Modified Animals

Animals may be made that are mono-allelic or bi-allelic for a chromosomal modification, using methods that either leave a marker in place, allow for it to be bred out of an animal, or by methods that do not place a marker in the animal. For instance, the inventors have used methods of homologous dependent recombination (HDR) to make changes to, or insertion of exogenous genes into, chromosomes of animals. Tools such as siste-specific nucleases, e.g., TALENs, zinc finger nucleases (ZFN), or CRISPR, and recombinase fusion proteins, as well as conventional methods, are available.

The term natural allele in the context of genetic modification means an allele found in nature in the same species of organism that is being modified. The term novel allele means a non-natural allele. A human allele placed into a goat is a novel allele. Thus a natural allele is a variation already existing within a species that can be interbred. And a novel allele is one that does not exist within a species that can be interbred. Movement of an allele interspecies means from one species of animal to another and movement intraspecies means movement between animals of the same species.

Moving an allele from one breed to another by conventional breeding processes involves swapping many alleles between the breeds. Recombination during meiosis inevitably exchanges genetic loci between the breeds. In contrast, site-specific nuclease modified livestock and other animals are free of genetic changes that result from meiotic recombination events since the cells or embryos are modified at a time when cells are exclusively mitotic. As a result, a TALEN-modified animal can easily be distinguished from an animal created by sexual reproduction.

The processes herein provide for editing the genomes of existing animals. The animal has a fixed phenotype and cloning the animal, e.g., by somatic cell cloning, effectively preserves that phenotype. Making a specific change or changes in a cellular genome during cloning allows for a known phenotype to be altered. Processes herein alternatively provide for altering a genome of an embryo that has yet to develop into an animal with fixed traits. Embryos with sound genetics may nonetheless not express all of the traits that are within the genetic potential of their genetics, i.e., animals do not always express the traits that their line is bred for.

The inventors have previously demonstrated effective cloning efficiency when cloning from polygenic populations of modified cells (Carlson et al., 2011). Additionally, however, TALEN-mediated genome modification, as well as modification by recombinase fusion molecules, provides for a bi-allelic alteration to be accomplished in a single generation. For example, an animal homozygous for a knocked-out gene may be made by SCNT and without inbreeding to produce homozygosity. Gestation length and maturation to reproduction age for livestock such as pigs and cattle is a significant barrier to research and to production. For example, generation of a homozygous knockout from heterozygous mutant cells (both sexes) by cloning and breeding would require 16 and 30 months for pigs and cattle respectively.

The inventors have previously shown that transgenic primary fibroblasts can be effectively expanded and isolated as colonies when plated with non-transgenic fibroblasts and subjected to drug selection using a transposon co-selection technique (Carlson et al., 2011, U.S. Pub. No. 2011/0197290). It was further shown (see US 2012/0222143) that puromycin resistant colonies were isolated for cells treated with six TALEN pairs and evaluated their genotypes by SURVEYOR assay or direct sequencing of PCR products spanning the target site. In general, the proportion of indel positive clones was similar to predictions made based on day 3 modification levels. Bi-allelic knockout clones were identified for 5 of 6 TALEN pairs, occurring in up to 35% of indel positive cells. Notably, the frequency of bi-allelic knockout clones for the majority of TALEN pairs exceeds what would be predicted if the cleavage of each chromosome is treated as an independent event.

TALEN-induced homologous recombination eliminates the need for linked selection markers. TALENs may be used to precisely transfer specific alleles into a livestock genome by homology dependent repair (HDR). In a pilot study, a specific 11 bp deletion (the Belgian Blue allele) (Grobet et al., 1997; Kambadur et al., 1997) was introduced into the bovine GDF8 locus (see US 2012/0222143). When transfected alone, the btGDF8.1 TALEN pair cleaved up to 16% of chromosomes at the target locus. Co-transfection with a supercoiled homologous DNA repair template harboring the 11 bp deletion resulted in a gene conversion frequency (HDR) of up to 5% at day 3 without selection for the desired event. Gene conversion was identified in 1.4% of isolated colonies that were screened.

TALENs

TALENs are genetic engineering tools. Inactivation of a gene is one of many uses of TALENs. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA.

Miller et al. (Miller et al. (2011) *Nature Biotechnol* 29:143) reported making TALENs for site-specific nuclease architecture by linking TAL truncation variants to the catalytic domain of FokI nuclease. The resulting TALENs were shown to induce gene modification in immortalized human cells by means of the two major eukaryotic DNA repair pathways, non-homologous end joining (NHEJ) and homology directed repair. The TALENs can be engineered for specific binding. Improvements of the Miller et al. TALENS are described in U.S. Ser. No. 13/594,694 filed Aug. 24, 2012. Specific binding, as that term is commonly used in the biological arts, refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions.

The cipher for TALs has been reported (PCT Application WO 2011/072246) wherein each DNA binding repeat is responsible for recognizing one base pair in the target DNA sequence. The residues may be assembled to target a DNA sequence, with: (a) HD for recognition of C/G; (b) NI for recognition of A/T; (c) NG for recognition of T/A; (d) NS for recognition of C/G or A/T or T/A or G/C; (e) NN for recognition of G/C or A/T; (f) IG for recognition of T/A; (g) N for recognition of C/G; (h) HG for recognition of C/G or T/A; (i) H for recognition of T/A; and (j) NK for recognition of G/C. In brief, a target site for binding of a TALEN is determined and a fusion molecule comprising a nuclease and a series of RVDs that recognize the target site is created. Upon binding, the nuclease cleaves the DNA so that cellular repair machinery can operate to make a genetic modification at the cut ends. The term TALEN means a protein comprising a Transcription Activator-like (TAL) effector binding domain and a nuclease domain and includes monomeric TALENs that are functional per se as well as others that require dimerization with another monomeric TALEN. The dimerization can result in a homodimeric TALEN when both monomeric TALEN are identical or can result in a heterodimeric TALEN when monomeric TALEN are different.

In some embodiments, a monomeric TALEN can be used. TALEN typically function as dimers across a bipartite recognition site with a spacer, such that two TAL effector domains are each fused to a catalytic domain of the FokI restriction enzyme, the DNA-recognition sites for each resulting TALEN are separated by a spacer sequence, and binding of each TALEN monomer to the recognition site allows FokI to dimerize and create a double-strand break within the spacer. Monomeric TALENs also can be constructed, however, such that single TAL effectors are fused to a nuclease that does not require dimerization to function. One such nuclease, for example, is a single-chain variant of FokI in which the two monomers are expressed as a single polypeptide. Other naturally occurring or engineered monomeric nucleases also can serve this role. The DNA recognition domain used for a monomeric TALEN can be derived from a naturally occurring TAL effector. Alternatively, the DNA recognition domain can be engineered to recognize a specific DNA target. Engineered single-chain TALENs may be easier to construct and deploy, as they require only one engineered DNA recognition domain. A dimeric DNA sequence-specific nuclease can be generated using two different DNA binding domains (e.g., one TAL effector binding domain and one binding domain from another type of molecule). TALENs may function as dimers across a bipartite recognition site with a spacer. This nuclease architecture also can be used for target-specific nucleases generated from, for example, one TALEN monomer and one zinc finger nuclease monomer. In such cases, the DNA recognition sites for the TALEN and zinc finger nuclease monomers can be separated by a spacer of appropriate length. Binding of the two monomers can allow FokI to dimerize and create a double-strand break within the spacer sequence. DNA binding domains other than zinc fingers, such as homeodomains, myb repeats or leucine zippers, also can be fused to FokI and serve as a partner with a TALEN monomer to create a functional nuclease.

In some embodiments, a TAL effector can be used to target other protein domains (e.g., non-nuclease protein domains) to specific nucleotide sequences. For example, a TAL effector can be linked to a protein domain from, without limitation, a DNA 20 interacting enzyme (e.g., a methylase, a topoisomerase, an integrase, a transposase, or a ligase), a transcription activators or repressor, or a protein that interacts with or modifies other proteins such as histones. Applications of such TAL effector fusions include, for example, creating or modifying epigenetic regulatory elements, making site-specific insertions, deletions, or repairs in DNA, controlling gene expression, and modifying chromatin structure.

The spacer of the target sequence can be selected or varied to modulate TALEN specificity and activity. The flexibility in spacer length indicates that spacer length can be chosen to target particular sequences with high specificity. Further, the variation in activity has been observed for different spacer lengths indicating that spacer length can be chosen to achieve a desired level of TALEN activity.

The term nuclease includes exonucleases and endonucleases. The term endonuclease refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII, NotI, BbvCI, EcoRI, BglII, and AlwI. Endonucleases comprise also rare-cutting endonucleases when having typically a polynucleotide recognition site of about 12-45 basepairs (bp) in length, more preferably of 14-45 bp. Rare-cutting endonucleases induce DNA double-strand breaks (DSBs) at a defined locus. Rare-cutting endonucleases can for example be a homing endonuclease, a chimeric Zinc-Finger nuclease (ZFN) resulting from the fusion of engineered zinc-finger domains with the catalytic domain of a restriction enzyme such as FokI or a chemical endonuclease. In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences. Such chemical endonucleases are comprised in the term "endonuclease" according to the present invention. Examples of such endonuclease include I-See I, I-Chu L I-Cre I, I-Csm I, PI-See L PI-Tti L PI-Mtu I, I-Ceu I, I-SceI I, I-SceIII, HO, PI-Civ I, PI-Ctr I, PI-Aae I, PI-Bsu I, PI-Dha I, PI-Dra I, PI-May I, PI-Meh I, PI-Mfu I, PI-Mfl I, PI-Mga I, PI-Mgo I, PI-Min I, PI-Mka I, PI-Mle I, PI-Mma I, PI-30 Msh I, PI-Msm I, PI-Mth I, PI-Mtu I, PI-Mxe I, PI-Npu I, PI-Pfu I, PI-Rma I, PI-Spb I, PI-Ssp I, PI-Fae I, PI-Mja I, PI-Pho I, PI-Tag I, PI-Thy I, PI-Tko I, PI-Tsp I, I-MsoI.

A genetic modification made by TALENs or other tools may be, for example, chosen from the list consisting of an insertion, a deletion, insertion of an exogenous nucleic acid fragment, and a substitution. The term "insertion" is used broadly to mean either literal insertion into the chromosome or use of the exogenous sequence as a template for repair. In general, a target DNA site is identified and a TALEN-pair is created that will specifically bind to the site. The TALEN is delivered to the cell or embryo, e.g., as a protein, mRNA or by a vector that encodes the TALEN. The TALEN cleaves the DNA to make a double-strand break that is then repaired, often resulting in the creation of an indel, or incorporating sequences or polymorphisms contained in an accompanying exogenous nucleic acid that is either inserted into the chromosome or serves as a template for repair of the break with a modified sequence. This template-driven repair is a useful process for changing a chromosome, and provides for effective changes to cellular chromosomes.

The term exogenous nucleic acid means a nucleic acid that is added to the cell or embryo, regardless of whether the nucleic acid is the same or distinct from nucleic acid sequences naturally in the cell. The term nucleic acid or nucleic acid fragment or nucleic acid sequence is broad and includes a chromosome, expression cassette, gene, DNA, RNA, mRNA, or portion thereof. The cell or embryo may be, for instance, chosen from the group consisting of livestock, an artiodactyl, a cow, a swine, a sheep, a goat, a chicken, a rabbit, and a fish. The term livestock means domesticated animals that are raised as commodities for food or biological material. The term artiodactyl means a hoofed mammal of the order Artiodactyla, which includes cattle, deer, camels, hippopotamuses, sheep, and goats, that have an even number of toes, usually two or sometimes four, on each foot.

Some embodiments involve a composition or a method of making a genetically modified livestock and/or artiodactyl comprising introducing a TALEN-pair into livestock and/or an artiodactyl cell or embryo that makes a genetic modification to DNA of the cell or embryo at a site that is specifically bound by the TALEN-pair, and producing the livestock animal/artiodactyl from the cell. Direct injection may be used for the cell or embryo, e.g., into a zygote, blastocyst, or embryo. Alternatively, the TALEN and/or other factors may be introduced into a cell using any of many known techniques for introduction of proteins, RNA, mRNA, DNA, or vectors. Genetically modified animals may be made from the embryos or cells according to known processes, e.g., implantation of the embryo into a gestational host, or various cloning methods. The phrase "a genetic modification to DNA of the cell at a site that is specifically bound by the TALEN", or the like, means that the genetic modification is made at the site cut by the nuclease on the TALEN when the TALEN is specifically bound to its target site. The nuclease does not cut exactly where the TALEN-pair binds, but rather at a defined site between the two binding sites.

Some embodiments involve a composition or a treatment of a cell that is used for cloning the animal. The cell may be a livestock and/or artiodactyl cell, a cultured cell, a primary cell, a primary somatic cell, a zygote, a germ cell, a primordial germ cell, or a stem cell. For example, an embodiment is a composition or a method of creating a genetic modification comprising exposing a plurality of primary cells in a culture to TALEN proteins or a nucleic acid encoding a TALEN or TALENs. The TALENs may be introduced as proteins or as nucleic acid fragments, e.g., encoded by mRNA or a DNA sequence in a vector.

Genetic modification of cells may also include insertion of a reporter. The reporter may be, e.g., a florescent marker, e.g., green fluorescent protein and yellow fluorescent protein. The reporter may be a selection marker, e.g., puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), or xanthin-guanine phosphoribosyltransferase (XGPRT). Vectors for the reporter, selection marker, and/or one or more TALEN may be a plasmid, transposon, transposase, viral, or other vectors, e.g., as detailed herein.

TALENs may be directed to a plurality of DNA sites. The sites may be separated by several thousand or many thousands of base pairs. The DNA can be rejoined by cellular machinery to thereby cause the deletion of the entire region between the sites. Embodiments include, for example, sites separated by a distance between 1-5 megabases or between 50% and 80% of a chromosome, or between about 100 and about 1,000,000 basepairs; artisans will immediately appreciate that all the ranges and values within the explicitly stated ranges are contemplated, e.g., from about 1,000 to about 10,000 basepairs or from about 500 to about 500,000 basepairs. Alternatively, exogenous DNA may be added to the cell or embryo for insertion of the exogenous DNA, or template-driven repair of the DNA between the sites. Modification at a plurality of sites may be used to make genetically modified cells, embryos, artiodactyls, and livestock.

Zinc Finger Nucleases

Zinc-finger nucleases (ZFNs) are artificial restriction enzymes generated by fusing a zinc finger DNA-binding domain to a DNA-cleavage domain. Zinc finger domains can be engineered to target desired DNA sequences and this enables zinc-finger nucleases to target unique sequences within complex genomes. By taking advantage of endogenous DNA repair machinery, these reagents can be used to alter the genomes of higher organisms. ZFNs may be used in method of inactivating genes.

A zinc finger DNA-binding domain has about 30 amino acids and folds into a stable structure. Each finger primarily binds to a triplet within the DNA substrate. Amino acid residues at key positions contribute to most of the sequence-specific interactions with the DNA site. These amino acids can be changed while maintaining the remaining amino acids to preserve the necessary structure. Binding to longer DNA sequences is achieved by linking several domains in tandem. Other functionalities like non-specific FokI cleavage domain (N), transcription activator domains (A), transcription repressor domains (R) and methylases (M) can be fused to a ZFPs to form ZFNs respectively, zinc finger transcription activators (ZFA), zinc finger transcription repressors (ZFR, and zinc finger methylases (ZFM). Materials and methods for using zinc fingers and zinc finger nucleases for making genetically modified animals are disclosed in, e.g., U.S. Pat. No. 8,106,255 US20120192298, US20110023159, and US20110281306.

Clustered Regularly Interspaced Short Palindromic Repeats

Clustered regularly interspaced short palindromic repeats (CRISPR) are derived from bacterial/archea adaptive immune defenses. CRISPR activity involves integration of "spacers" from invading virus or plasmid DNA into the CRISPR locus, expression and processing of short guiding CRISPR RNAs (crRNAs) consisting of spacer-repeat units, and cleavage of nucleic acids complementary to the spacer. The nuclease Cas9 searches for sequences matching the crRNA to cleave. Cas9 cuts the DNA only if a correct protospacer adjacent motif (PAM) is also present at the 3' end. As a genome engineering tool, the specificity of gRNA-directed Cas9 cleavage is very helpful.

For instance, DiCarlo et al. (Nucl. Acids Res. 41(5) (2013)) reported that the CRISPR-Cas components, Cas9 gene and a designer genome targeting CRISPR guide RNA (gRNA), showed robust and specific RNA-guided endonuclease activity at targeted endogenous genomic loci in yeast. Using constitutive Cas9 expression and a transient gRNA cassette, they showed that targeted double-strand breaks increased homologous recombination rates of single- and double-stranded oligonucleotide donors by 5-fold and 130-fold, respectively. In addition, co-transformation of a gRNA plasmid and a donor DNA in cells constitutively expressing Cas9 resulted in near 100% donor DNA recombination frequency. The term CRISPR herein is used to refer to the genetic engineering tools that use these techniques.

And Cong et al. reported that CRISPR systems and associated Cas9 nucleases could be directed by short RNAs to induce precise cleavage at endogenous genomic loci in human and mouse cells. Cas9 were also converted into a nicking enzyme to facilitate homology-directed repair with minimal mutagenic activity. Finally, multiple guide sequences were capable of being encoded into a single CRISPR array to enable simultaneous editing of several sites within the mammalian genome, demonstrating easy programmability and wide applicability of the CRISPR technology.

Vectors and Nucleic Acids

A variety of nucleic acids may be introduced into the artiodactyl or other cells, for knockout purposes, for inactivation of a gene, to obtain expression of a gene, or for other purposes. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7(3):187; and Hyrup et al. (1996) *Bioorgan. Med. Chem.* 4:5. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, inducible promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes or heart tissue and can include the albumin or alpha-myosin heavy chain promoters, respectively. In other embodiments, a promoter that facilitates the expression of a nucleic acid molecule without significant tissue- or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. In some embodiments, a fusion of the chicken beta actin gene promoter and the CMV enhancer is used as a promoter. See, for example, Xu et al. (2001) *Hum. Gene Ther.* 12:563; and Kiwaki et al. (1996) *Hum. Gene Ther.* 7:821.

An example of an inducible promoter is the tetracycline (tet)-on promoter system, which can be used to regulate transcription of the nucleic acid. In this system, a mutated Tet repressor (TetR) is fused to the activation domain of herpes simplex virus VP16 trans-activator protein to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

In some embodiments, a sequence encoding a selectable marker can be flanked by recognition sequences for a recombinase such as, e.g., Cre or Flp. For example, the selectable marker can be flanked by loxP recognition sites (34-bp recognition sites recognized by the Cre recombinase) or FRT recognition sites such that the selectable marker can be excised from the construct. See, Orban, et al., *Proc. Natl. Acad. Sci.* (1992) 89:6861, for a review of Cre/lox technology, and Brand and Dymecki, *Dev. Cell* (2004) 6:7. A transposon containing a Cre- or Flp-activatable transgene interrupted by a selectable marker gene also can be used to obtain transgenic animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

In some embodiments, the exogenous nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™ tag (Kodak, New Haven, Conn.).

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult artiodactyl cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to an exogenous nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) *Nucleic Acids Res.* 31:6873); Tol2 (Kawakami (2007) *Genome Biology* 8(Suppl.1):S7; Minos (Pavlopoulos et al. (2007) *Genome Biology* 8(Suppl.1):S2); Hsmar1 (Miskey et al. (2007)) *Mol Cell Biol.* 27:4589); and Passport have been developed to introduce nucleic acids into cells, including mice, human, and pig cells. The Sleeping Beauty transposon is particularly useful. A transposase can be delivered as a protein, encoded on the same nucleic acid construct as the exogenous nucleic acid, can be introduced on a separate nucleic acid construct, or provided as an mRNA (e.g., an in vitro-transcribed and capped mRNA).

Insulator elements also can be included in a nucleic acid construct to maintain expression of the exogenous nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region-(MAR) type insulator elements and border-type insulator elements. See, for example, U.S. Pat. Nos. 6,395,549, 5,731,178, 6,100,448, and 5,610,053, and U.S. Publication No. 2004/0203158.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). The term transgenic is used broadly herein and refers to a genetically modified organism or genetically engineered organism whose genetic material has been altered using genetic engineering techniques. A knockout artiodactyl is thus transgenic regardless of whether or not exogenous genes or nucleic acids are expressed in the animal or its progeny.

Genetically Modified Animals

Animals may be modified using TALENs, Zinc Fingers, CRISPR/Cas9, or other genetic engineering tools, including recombinase fusion proteins, or various vectors that are known. Materials and Methods of genetically modifying animals are further detailed in US 2012/0222143, US 2012/0220037 and 2010/0251395 filed Nov. 10, 2009 which are hereby incorporated herein by reference for all purposes; in case of conflict, the instant specification is controlling. The term trans-acting refers to processes acting on a target gene from a different molecule (i.e., intermolecular). A trans-acting element is usually a DNA sequence that contains a gene. This gene codes for a protein (or microRNA or other diffusible molecule) that is used in the regulation the target gene. The trans-acting gene may be on the same chromosome as the target gene, but the activity is via the intermediary protein or RNA that it encodes. Inactivation of a gene using a dominant negative generally involves a trans-acting element. The term cis-regulatory or cis-acting means an action without coding for protein or RNA; in the context of gene inactivation, this generally means inactivation of the coding portion of a gene, or a promoter and/or operator that is necessary for expression of the functional gene.

Various techniques known in the art can be used to introduce nucleic acid constructs into animals to produce founder animals and to make animal lines, nucleic acid construct (or a knock-out of a gene) is integrated into the genome. Such techniques include, without limitation, pronuclear microinjection (U.S. Pat. No. 4,873,191), retrovirus mediated gene transfer into germ lines (Van der Putten et al. (1985) *Proc. Natl. Acad. Sci. USA* 82, 6148-1652), gene targeting into embryonic stem cells (Thompson et al. (1989) *Cell* 56, 313-321), electroporation of embryos (Lo (1983) *Mol. Cell. Biol.* 3, 1803-1814), sperm-mediated gene transfer (Lavitrano et al. (2002) *Proc. Natl. Acad. Sci. USA* 99, 14230-14235; Lavitrano et al. (2006) *Reprod. Fert. Develop.* 18, 19-23), and in vitro transformation of somatic cells, such as cumulus or mammary cells, or adult, fetal, or embryonic stem cells, followed by nuclear transplantation (Wilmut et al. (1997) *Nature* 385, 810-813; and Wakayama et al. (1998) *Nature* 394, 369-374). Pronuclear microinjection, sperm mediated gene transfer, and somatic cell nuclear transfer are particularly useful techniques. An animal that is genomically modified is an animal wherein all of its cells have the genetic modification, including its germ line cells. When methods are used that produce an animal that is mosaic in its genetic modification, the animals may be inbred and progeny that are genomically modified may be selected. Cloning, for instance, may be used to make a mosaic animal if its cells are modified at the blastocyst state, or genomic modification can take place when a single-cell is modified. Animals that are modified so they do not sexually mature can be homozygous or heterozygous for the modification, depending on the specific approach that is used. If a particular gene is inactivated by a knock out modification, homozygousity would normally be required. If a particular gene is inactivated by an RNA interference or dominant negative strategy, then heterozygosity is often adequate.

Typically, in pronuclear microinjection, a nucleic acid construct is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 OOCYTE MATURATION MEDIUM (Minitube, Verona, Wis.) supplemented with 0.1 mg/mL cysteine, 10 ng/mL epidermal growth factor, 10% porcine follicular fluid, 50 µM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium, which will not contain cAMP, PMSG or hCG and incubated for an additional 22 hours. Matured oocytes can be stripped of their cumulus cells by vortexing in 0.1% hyaluronidase for 1 minute.

For swine, mature oocytes can be fertilized in 500 µl Minitube PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to $4 \times 10^5$ sperm. Sperm concentrations can be analyzed by computer assisted semen analysis (SPERMVISION, Minitube, Verona, Wis.). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs can be injected into one of the pronuclei. Then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with using an Eppendorf FEMTOJET injector and can be cultured until blastocyst formation. Rates of embryo cleavage and blastocyst formation and quality can be recorded.

Embryos can be surgically transferred into uteri of asynchronous recipients. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed.

In somatic cell nuclear transfer, a transgenic artiodactyl cell (e.g., a transgenic pig cell or bovine cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis-2 are termed eggs. After producing a porcine or bovine embryo (e.g., by fusing and activating the oocyte), the embryo is transferred to the oviducts of a recipient female, about 20 to 24 hours after activation. See, for example, Cibelli et al. (1998) *Science* 280, 1256-1258 and U.S. Pat. No. 6,548,741. For pigs, recipient females can be checked for pregnancy approximately 20-21 days after transfer of the embryos. Other livestock have comparable processes.

Standard breeding techniques can be used to create animals that are homozygous for the exogenous nucleic acid from the initial heterozygous founder animals. Homozygosity may not be required, however. Modified animals pigs described herein can be bred with other animals of interest.

In some embodiments, a nucleic acid of interest and a selectable marker can be provided on separate transposons and provided to either embryos or cells in unequal amount, where the amount of transposon containing the selectable marker far exceeds (5-10 fold excess) the transposon containing the nucleic acid of interest. Transgenic cells or animals expressing the nucleic acid of interest can be isolated based on presence and expression of the selectable marker. Because the transposons will integrate into the genome in a precise and unlinked way (independent transposition events), the nucleic acid of interest and the selectable marker are not genetically linked and can easily be separated by genetic segregation through standard breeding. Thus, transgenic animals can be produced that are not constrained to retain selectable markers in subsequent generations, an issue of some concern from a public safety perspective.

Once transgenic animal have been generated, expression of an exogenous nucleic acid can be assessed using standard techniques. Initial screening can be accomplished by Southern blot analysis to determine whether or not integration of the construct has taken place. For a description of Southern analysis, see sections 9.37-9.52 of Sambrook et al., 1989, *Molecular Cloning, A Laboratory Manual*, second edition, Cold Spring Harbor Press, Plainview; NY. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example *PCR Primer: A Laboratory Manual*, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) *Genetic Engineering News* 12,1; Guatelli et al. (1990) *Proc. Natl. Acad. Sci. USA* 87:1874; and Weiss (1991) *Science* 254:1292. At the blastocyst stage, embryos can be individually processed for analysis by PCR, Southern hybridization and splinkerette PCR (see, e.g., Dupuy et al. *Proc Natl Acad Sci USA* (2002) 99:4495).

Expression of a nucleic acid sequence encoding a polypeptide in the tissues of transgenic animals can be assessed using techniques that include, for example, Northern blot analysis of tissue samples obtained from the animal, in situ hybridization analysis, Western analysis, immunoassays such as enzyme-linked immunosorbent assays, and reverse-transcriptase PCR (RT-PCR).

Founder Animals, Animal Lines, Traits, and Reproduction

Founder animals may be produced by cloning and other methods described herein. The founders can be homozygous for a genetic modification, as in the case where a zygote or a primary cell undergoes a homozygous modification. Similarly, founders can also be made that are heterozygous. The founders may be genomically modified, meaning that all of the cells in their genome have undergone modification. Founders can be mosaic for a modification, as may happen when vectors are introduced into one of a plurality of cells in an embryo, typically at a blastocyst stage. Progeny of mosaic animals may be tested to identify progeny that are genomically modified. An animal line is established when a pool of animals has been created that can be reproduced sexually or by assisted reproductive techniques, with heterogeneous or homozygous progeny consistently expressing the modification.

In livestock, many alleles are known to be linked to various traits such as production traits, type traits, workability traits, and other functional traits. Artisans are accustomed to monitoring and quantifying these traits, e.g., Visscher et al., Livestock Production Science, 40 (1994) 123-137, U.S. Pat. No. 7,709,206, US 2001/0016315, US 2011/0023140, and US 2005/0153317. An animal line may include a trait chosen from a trait in the group consisting of a production trait, a type trait, a workability trait, a fertility trait, a mothering trait, and a disease resistance trait. Further traits include expression of a recombinant gene product.

Recombinases

Embodiments of the invention include administration of a TALEN or TALENs or a Zinc finger nuclease with a recombinase or other DNA-binding protein associated with DNA recombination. Embodiments also include administration of a recombinase fusion protein to create a double stranded break in a cellular chromosome, e.g., a RecA-gal4 fusion, as in U.S. Pub. No 2011/0059160.

A recombinase forms a filament with a nucleic acid fragment and, in effect, searches cellular DNA to find a DNA sequence substantially homologous to the sequence. An embodiment of a TALEN-recombinase embodiment comprises combining a recombinase with a nucleic acid sequence that serves as a template. The template sequence has substantial homology to a site that is targeted for cutting by the TALEN/TALEN pair. As described herein, the template sequence provides for a change to the native DNA, by placement of an allele, creation of an indel, insertion of exogenous DNA, or with other changes. The TALEN is placed in the cell or embryo by methods described herein as a protein, mRNA, or by use of a vector. The recombinase is combined with the template sequence to form a filament and placed into the cell. The recombinase and/or template sequence that combines with the recombinase may be placed in the cell or embryo as a protein, an mRNA, or with a vector that encodes the recombinase. The disclosure of US Pub 2011/0059160 is hereby incorporated herein by reference for all purposes; in case of conflict, the specification is controlling. The term recombinase refers to a genetic recombination enzyme that enzymatically catalyzes, in a cell, the joining of relatively short pieces of DNA between two relatively longer DNA strands. Recombinases include Cre recombinase, Hin recombinase, RecA, RAD51, Cre, and FLP. Cre recombinase is a Type I topoisomerase from P1 bacteriophage that catalyzes site-specific recombination of DNA between loxP sites. Hin recombinase is a 21 kD protein composed of 198 amino acids that is found in the bacteria *Salmonella*. Hin belongs to the serine recombinase family of DNA invertases in which it relies on the active site serine to initiate DNA cleavage and recombination. RAD51 is a human gene. The protein encoded by this gene is a member of the RAD51 protein family which assist in repair of DNA double strand breaks. RAD51 family members are homologous to the bacterial RecA and yeast Rad51. Cre recombinase is an experimental enzyme that in lab tests has successfully removed DNA inserted by HIV from infected cells. The enzyme was derived from Cre recombinase through selective mutation for the purposes of identifying HIV markers, which are not bounded by loxP sites and therefore disallow attempts at Cre-Lox recombination. FLP refers to Flippase recombination enzyme (FLP or Flp) derived from the 2μ plasmid of the baker's yeast Saccharomyces cerevisiae.

A eukaryotic homologue of RecA, also possessing recombinase activity, is the Rad51 protein, first identified in the yeast Saccharomyces cerevisiae. See Bishop et al., (1992) Cell 69: 439-56 and Shinohara et al, (1992) Cell: 457-70 Aboussekhra, et al., (1992) Mol. Cell. Biol. 72, 3224-3234. Basile et al., (1992) Mol. Cell. Biol. 12, 3235-3246 Plant Rad51 sequences are described in U.S. Pat. Nos. 6,541,684; 6,720,478; 6,905,857 and 7,034,117. Another yeast protein that is homologous to RecA is the Dmc1 protein. RecA/Rad51 homologues in organisms other than E. coli and S. cerevisiae have been described. Morita et al. (1993) Proc. Natl. Acad. Sci. USA 90:6577-6580; Shinohara et al. (1993) Nature Genet. 4:239-243; Heyer (1994) Experientia 50:223-233; Maeshima et al. (1995) Gene 160:195-200; U.S. Pat. Nos. 6,541,684 and 6,905,857.

Herein, "RecA" or "RecA protein" refers to a family of RecA-like recombination proteins having essentially all or most of the same functions, particularly: (i) the ability to position properly oligonucleotides or polynucleotides on their homologous targets for subsequent extension by DNA polymerases; (ii) the ability topologically to prepare duplex nucleic acid for DNA synthesis; and, (iii) the ability of RecA/oligonucleotide or RecA/polynucleotide complexes efficiently to find and bind to complementary sequences. The best characterized RecA protein is from E. coli; in addition to the original allelic form of the protein a number of mutant RecA-like proteins have been identified, for example, RecA803. Further, many organisms have RecA-like strand-transfer proteins including, for example, yeast, Drosophila, mammals including humans, and plants. These proteins include, for example, Rec1, Rec2, Rad51, Rad51B, Rad51C, Rad51D, Rad51E, XRCC2 and DMC1. An embodiment of the recombination protein is the RecA protein of E. coli. Alternatively, the RecA protein can be the mutant RecA-803 protein of E. coli, a RecA protein from another bacterial source or a homologous recombination protein from another organism.

A nucleoprotein filament, or "filament" may be formed. The term filament, in the context of forming a structure with a recombinase, is a term known to artisans in these fields. The nucleoprotein filament so formed can then be, e.g., contacted with another nucleic acid or introduced into a cell. Methods for forming nucleoprotein filaments, wherein the filaments comprise polypeptide sequences having recombinase activity and a nucleic acid, are well-known in the art. See, e.g., Cui et al. (2003) Marine Biotechnol. 5:174-184 and U.S. Pat. Nos. 4,888,274; 5,763,240; 5,948,653 and 7,199,281, the disclosures of which are incorporated by reference for the purposes of disclosing exemplary techniques for binding recombinases to nucleic acids to form nucleoprotein filaments.

In general, a molecule having recombinase activity is contacted with a linear, single-stranded nucleic acid. The linear, single-stranded nucleic acid may be a probe. The methods of preparation of such single stranded nucleic acids are known. The reaction mixture typically contains a magnesium ion. Optionally, the reaction mixture is buffered and optionally also contains ATP, dATP or a nonhydrolyzable ATP analogue, such as, for example, γ-thio-ATP (ATP-γ-S) or γ-thio-GTP (GTP-γ-S). Reaction mixtures can also optionally contain an ATP-generating system. Double-stranded DNA molecules can be denatured (e.g., by heat or alkali) either prior to, or during, filament formation. Optimization of the molar ratio of recombinase to nucleic acid is within the skill of the art. For example, a series of different concentrations of recombinase can be added to a constant amount of nucleic acid, and filament formation assayed by mobility in an agarose or acrylamide gel. Because bound protein retards the electrophoretic mobility of a polynucleotide, filament formation is evidenced by retarded mobility of the nucleic acid. Either maximum degree of retardation, or maximum amount of nucleic acid migrating with a retarded mobility, can be used to indicate optimal recombinase: nucleic acid ratios. Protein-DNA association can also be quantitated by measuring the ability of a polynucleotide to bind to nitrocellulose.

Polypeptides

In some cases a determination of the percent identity of a peptide to a sequence set forth herein may be required. In such cases, the percent identity is measured in terms of the number of residues of the peptide, or a portion of the peptide. A polypeptide of, e.g., 90% identity, may also be a portion of a larger peptide. Embodiments include such polypeptides that have the indicated identity and/or conservative substitution of sequence set forth herein.

The term isolated as used herein with reference to a polypeptide refers to a polypeptide that either has no naturally occurring counterpart (e.g., a peptidomimetic), or has been chemically synthesized and is thus substantially uncontaminated by other polypeptides, or has been separated or purified from other most cellular components by which it is naturally accompanied (e.g., other cellular proteins, polynucleotides, or cellular components).

REFERENCES

All of the following references are hereby incorporated herein by reference. Patents and patent applications set forth in this document are also hereby incorporated herein by reference.

In case of conflict, the instant specification is controlling.

1. Thompson, D., et al., *Economic costs of the foot and mouth disease outbreak in the United Kingdom in* 2001. Rev. Sci. Tech., 2002. 21: p. 657-687.
2. Grubman, M. J. and B. Baxt, *Foot-and-mouth disease.* Clin. Microbiol. Rev., 2004. 17: p. 465-493.
3. Cao, X., et al., *Functional analysis of the two alternative translation initiation sites of foot-and-mouth disease virus.* J. Virol., 1995. 69: p. 560-563.
4. Glaser, W. and T. Skern, *Extremely efficient cleavage of eIF4G by picornaviral proteinases L and 2A in vitro.* FEBS Lett., 2000. 480: p. 151-155.
5. Gradi, A., et al., *Cleavage of eukaryotic translation initiation factor 4GII within foot-and-mouth disease virus-infected cells: identification of the L-protease cleavage site in vitro.* J. Virol., 2004. 78: p. 3271-3278.
6. Hinton, T. M., et al., *Functional analysis of individual binding activities of the scaffold protein eIF4G.* J. biol. Chem., 2007. 282: p. 1695-1708.
7. Aitken, C. E. and J. R. Lorsch, *A mechanistic overview of translation initiation in eukaryotes.* Nature Rev. Struc. Mol. Biol., 2012. 19: p. 568-576.
8. Kerekatte, V., et al., *Cleavage of Poly(A)-binding protein by coxsackievirus 2A protease in vitro and in vivo: another mechanism for host protein synthesis shutoff?* J. Virol., 1999. 73: p. 709-717.

9. Foeger, N., et al., *The binding of foot-and-mouth disease virus leader proteinase to eIF4GI involves conserved ionic interactions.* FEBS J., 2005. 272: p. 2602-2611.
10. Prevot, D., J. L. Darlix, and T. Ohlmann, *Conducting the initiation of protein synthesis: the role of eIF4G.* Biol. Cell., 2003. 95: p. 141-156.
11. Lloyd, R. E., *Translational control by viral proteinases.* Virus Res., 2006. 119: p. 76-88.
12. Truniger, V. and M. A. Aranda, *Recessive resistance to plant viruses.* Adv. Virus Res., 2009. 75: p. 120-159.
13. de los Santos, T., et al., *The leader proteinase of foot-and-mouth disease virus inhibits the induction of beta interferon mRNA and blocks the host innate immune response.* J. Virol., 2006. 80: p. 1906-1914.
14. Perez-Martin, E., et al., *Bovine type III interferon significantly delays and reduces the severity of foot-and-mouth disease in cattle.* J. Virol., 2012. 86: p. 4477-4487.
15. Wang, D., et al., *The leader proteinase of foot-and-mouth disease virus negatively regulates the interferon pathway by acting as a viral deubiquitinase.* J. Virol., 2011. 85: p. 3758-3766.
16. Wang, D., et al., *Foot-and-mouth disease virus leader proteinase inhibits dsRNA-induced type I interferon transcription by decreasing interferon regulatory factor 3/7 in protein levels.* Biochem. Biophys. Res. Comm., 2010. 399: p. 72-78.
17. de los Santos, T., F. Diaz-San Segundo, and M. J. Grubman, *Degradation of nuclear factor kappa B during foot-and-mouth disease virus infection.* J. Virol., 2007. 81: p. 12803-12815.
18. Borman, A. M., et al., *eIF4G and its proteolytic cleavage products: effect on initiation of protein synthesis from capped, uncapped, and IRES-containing mRNAs.* RNA, 1997. 3: p. 186-196.
19. Zhao, X., et al., *Protection of cap-dependent protein synthesis in vivo and in vitro with an eIF4G-1 variant highly resistant to cleavage by Coxsackievirus 2A protease.* J. Biol. Chem., 2003. 278: p. 4449-4457.
20. Lopez de Quinto, S, and E. Martinez-Salas, *Interaction of the eIF4G initiation factor with the aphthovirus IRES is essential for internal translation initiation in vivo.* RNA, 2000. 6: p. 1380-1392.
21. Saleh, L., et al., *Functional interaction of translation initiation factor eIF4G with the foot-and-mouth disease virus internal ribosome entry site.* J. Gen. Virol., 2001. 82: p. 757-763.
22. Hinton, T. M., et al., *Conservation of L and 3C proteinase activities across distantly related aphthoviruses.* J. Gen. Virol., 2002. 83: p. 3111-3121.
23. Belsham, G. J., G. M. McInerney, and N. Ross-Smith, *Foot-and-mouth disease virus 3C protease induces cleavage of translation initiation factors eIF4A and eIF4G within infected cells.* J. Virol., 2000. 74: p. 272-280.
24. Strong, R. and G. J. Belsham, *Sequential modification of translation initiation factor eIF4GI by two different foot-and-mouth disease virus proteases within infected baby hamster kidney cells: identification of the 3 Cpro cleavage site.* J. Gen. Virol., 2004. 85: p. 2953-2962.
25. Piccone, M. E., et al., *The foot-and-mouth disease virus leader proteinase gene is not required for viral replication.* J. Virol., 1995. 69: p. 5372-5382.
26. Mason, P. W., et al., *Evaluation of a live-attenuated foot-and-mouth disease virus as a vaccine candidate.* Virology, 1997. 227: p. 96-102.
27. Chinsangaram, J., P. W. Mason, and M. J. Grubman, *Protection of swine by live and inactivated vaccines prepared from a leader proteinase-deficient serotype A12 foot-and-mouth disease virus.* Vaccine, 1998. 16: p. 1516-1522.
28. Chinsangaram, J., M. Koster, and M. J. Grubman, *Inhibition of L-deleted foot-and-mouths disease virus replication by alpha/beta interferon involves double-stranded RNA-dependent protein kinase.* J. Virol., 2001. 75: p. 5498-5503.
29. Fabian, M. R. and N. Sonenberg, *The mechanics of miRNA-mediated gene silencing: a look under the hood of miRISC.* Nature Rev. Struc. Mol. Biol., 2012. 19: p. 586-593.
30. Drake, J. W. and J. J. Holland, *Mutation rates among RNA viruses.* Proc Natl Acad Sci USA, 1999. 96: p. 13910-13913.
31. Pfeiffer, J. K. and K. Kirkegaard, *Increased fidelity reduces poliovirus fitness and virulence under selective pressure in mice.* PLoS Pathog., 2005. 1: p. e11.
32. Freistadt, M. S., J. A. Vaccaro, and K. E. Eberle, *Biochemical characterization of the fidelity of poliovirus RNA-dependent RNA polymerase.* Virol. J., 2007. 4: p. 44.
33. Lee, S. W., et al., *Attenuated vaccines can recombine to form virulent field viruses.* Science, 2012. 337: p. 188.
34. Carlson, D. F., S. C. Fahrenkrug, and P. B. Hackett, *Targeting DNA with fingers and TALENs.* Mol. Ther. Nuc. Acids, 2012. 1: p. e3.
35. Tan, S., et al., *Precision editing of large animal genomes.* Adv. Genet., 2012. 80: p. (in press).
36. Lamphear, B. J. and R. E. Rhoads, *A single amino acid change in protein synthesis initiation factor 4G renders cap-dependent translation resistant to picornaviral 2A proteases.* Biochemistry, 1996. 35: p. 15726-15733.
37. A. M. GEURTS, et al., Knockout rats via embryo microinjection of zinc-finger nucleases, 325 Science (2009).
38. I. D. CARBERY, et al., Targeted genome modification in mice using zinc-finger nucleases, 186 Genetics (2010).
39. Carlson, D. F., J. R. Garbe, et al. (2011). "Strategies for selection marker-free swine transgenesis using the Sleeping Beauty transposon system." Transgenic research 20(5): 1125-1137.
40. Carlson, D. F., W. Tan, et al. (2012). "Efficient TALEN-mediated gene knockout in livestock." Proceedings of the National Academy of Sciences of the United States of America 109(43): 17382-17387.
41. Guschin, D. Y., A. J. Waite, et al. (2010). "A rapid and general assay for monitoring endogenous gene modification." Methods in molecular biology 649: 247-256.

Patent applications: US 2010/0146655, US 2010/0105140, US 2011/0059160, US 2011/0197290, US 2010/0146655, US 2011/0197290, US 2012/0222143 and U.S. Ser. No. 61/662,767

EXAMPLES

Materials and methods, including making of TALENs, are generally as described in U.S. Ser. No. 13/594,694 filed Aug. 24, 2012, unless otherwise indicated. These processes have been demonstrated to be effective to change alleles in primary cells that are then used to make genetically modified founder animals that have the alleles and pass them to their progeny.

Example 1

Referring to FIG. 2, a portion of porcine EIF4GI is shown in panel A. The wild type sequence has asparagine and leucine residues in the minus 3 and 2 positions relative to the L$^{pro}$ cleavage site (arrowhead). In this example, the HDR template replaces the minus 3 and 2 residues with aspartic acid and phenylalanine to render the modified EIF4GI resistant to L$^{pro}$ cleavage. Two pairs of TALENs (top) were designed to cut the wild type EIF4GI to stimulate homologous recombination. Panel B: Surveyor (Cel-I) assay of pig fibroblasts transfected with each TALEN pair. Panel C: RFLP assay to determine the efficiency of homologous recombination.

Transfections were performed in early passage (<2 passages) primary pig fibroblasts. Fibroblasts at 70-90% confluence were harvested by for use in transfections. Two micrograms of TALEN mRNA ssEIF4G14.1 or ssEIF4G14.2 along with 0.2 nMole of a 90-mer homologous oligonucleotide (5'-cccagacttcactccgtcctttgccgacttcggccgac-cagcccttagcaaccgtgggcccccaaggggtgggccaggtggggagctgc c) (SEQ ID NO: 18) were transfected into 500,000 fibroblasts using the NEON nucleofection system (Life Technologies) with the following settings: 1 pulse, 1800 v; 20 ms width and a 100 µl tip. Transfected cells were cultured 3 days at either 30 degrees Celsius prior to indel analysis by the Surveyor assay (Transgenomic) (Carlson, Tan et al. 2012) and quantitative RFLP analysis using EagI. Products are resolved on a 10% PAGE gel and cleavage products are measured by densitometry. Percent NHEJ was calculated as described in Guischin et al. (Guschin, Waite et al. 2010) and displayed below. Percent homologous recombination was calculated by dividing the sum of cleavage product density by the sum of all products.

Additional L$^{pro}$ cleavage site mutations to EIF4GI may be introduced by the same methods in the future.

Example 2

For colony isolation, cells will be enumerated and plated at a range of densities 1-20 cells/cm² on 10 cm dishes. Cells will be cultured for 10-15 days until individual colonies of 3-4 mm in diameter are present. Individual colonies are aspirated with a p-200 pipettor under gentle aspiration and expelled into a well of 24-well plate with 500 µl of growth medium (Carlson, Garbe et al. 2011). Plates with clearly defined colonies (~10-30/plate) will be chosen for colony aspiration to limit the chance of aspirating cells from multiple colonies. Once a colony reaches 70-90 percent confluent in the 24-well dish, a portion will be harvested for RFPL analysis and the remainder will be cryopreserved. Cells will be taken from colonies that have been determined to have successfully acquired the intended features and used for cloning to make founder animals.

The specific embodiments above are intended to be illustrative and not limiting. Additional embodiments are within the broad concepts described herein. In addition, although the invention has been described with reference to particular embodiments, those skilled in the art will recognize that changes can be made in form and detail without departing from the spirit and scope of the invention. Any incorporation by reference of documents herein is limited such that no subject matter is incorporated that is contrary to the explicit disclosure herein.

The invention claimed is:

1. A gene edited pig whose genome comprises a modified eIF4GI gene, wherein said modified eIF4GI gene has the nucleotide sequence of SEQ ID NO: 2, wherein the modified eIF4GI gene expresses an altered eIF4GI protein relative to a wild type eIF4GI protein such that the gene edited pig is resistant to cleavage by a leader proteinase of foot-and-mouth disease virus enzyme ($L^{Pro}$).

2. The gene edited pig of claim 1, wherein the modified eIF4GI gene comprises an insertion, a deletion, or a substitution of one or more bases of the eIF4G gene.

3. The gene edited pig of claim 1, wherein the pig is from a first breed and the modified eIF4GI gene comprises a natural allele of the eIF4G gene found in another breed of pig.

4. The gene edited pig of claim 1, wherein the pig is a first species and the modified eIF4GI gene comprises an allele of the eIF4G gene in a second species.

5. The gene edited pig of claim 1, wherein the pig is homozygous for the modified eIF4G gene.

6. The gene edited pig of claim 1, wherein the pig is a founder animal.

7. The gene edited pig of claim 1, wherein the altered eIF4G protein is modified to prevent binding of (i) $L^{Pro}$ or (ii) $L^{Pro}$ and 3C protease of foot-and-mouth disease virus enzyme ($C^{Pro}$).

8. A method of producing a gene edited pig whose genome comprises a modified eIF4GI gene, wherein said modified eIF4GI gene has the nucleotide sequence of SEQ ID NO: 2, wherein the modified eIF4GI gene expresses an eIF4GI protein altered relative to a wild type eIF4GI protein such that the gene edited pig is resistant to cleavage by a leader proteinase of foot-and-mouth disease virus enzyme ($L^{Pro}$), the method comprising the steps of: (a) introducing into a pig fibroblast (i) a TALEN pair that specifically binds to the endogenous eIF4GI gene and causes a double-stranded DNA break to inactivate the eIF4GI gene in the pig fibroblast and (ii) a Homology-dependent repair (HDR) template comprising SEQ ID NO: 2; (b) permitting to occur homologous recombination events in the pig fibroblast; (c) transferring the transfected fibroblast into an enucleated pig recipient oocyte to generate a transgenic nuclear transfer embryo and activating said nuclear transfer embryo; and (d) transplanting the nuclear transfer embryo into a surrogate mother pig and permitting the implanted embryo to develop such that the transgenic pig whose genome comprises a modified eIF4GI gene is produced, wherein said pig expresses the modified eIF4GI gene and is resistant to cleavage by $L^{Pro}$.

9. The gene edited pig of claim 1, wherein the modified eIF4G gene is the only modification to the genome of said pig.

10. The method of claim 8, wherein the modified eIF4G gene is the only modification to the genome of the pig fibroblast.

* * * * *

SEQUENCE LISTING

```
<160> NUMBER OF SEQ ID NOS: 18

<210> SEQ ID NO 1
<211> LENGTH: 12
<212> TYPE: PRT
<213> ORGANISM: Sus scrofa

<400> SEQUENCE: 1

Pro Ser Phe Ala Asn Leu Gly Arg Pro Ala Leu Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: isoform for eIF4G

<400> SEQUENCE: 2

Pro Ser Phe Ala Asp Phe Gly Arg Pro Ala Leu Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: isoform of eIF4G

<400> SEQUENCE: 3

Pro Ser Phe Ala Asn Leu Gly Pro Pro Ala Leu Ser
1               5                   10

<210> SEQ ID NO 4
```

```
<211> LENGTH: 12
<212> TYPE: PRT
<213> ORGANISM: Artificial Sequence
<220> FEATURE:
<223> OTHER INFORMATION: isoform of eIF4G

<400> SEQUENCE: 4

Pro Ser Phe Ala Asn Phe Gly Arg Pro Ala Leu Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: isoform for eIF4G

<400> SEQUENCE: 5

Pro Ser Phe Ala Asn Asp Gly Arg Pro Ala Leu Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: isoform for eIF4G

<400> SEQUENCE: 6

Pro Ser Phe Ala Asn Pro Gly Arg Pro Ala Leu Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: isoform for eIF4G

<400> SEQUENCE: 7

Pro Ser Phe Ala Asn Tyr Gly Arg Pro Ala Leu Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: isoform eIF4G

<400> SEQUENCE: 8

Pro Ser Phe Ala Asn Trp Gly Arg Pro Ala Leu Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: isoform eIF4G

<400> SEQUENCE: 9

Pro Ser Phe Ala Asp Leu Gly Arg Pro Ala Leu Ser
1               5                   10

<210> SEQ ID NO 10
<211> LENGTH: 12
```

```
<212> TYPE: PRT
<213> ORGANISM: Artificial Sequence
<220> FEATURE:
<223> OTHER INFORMATION: isoform eIF4G

<400> SEQUENCE: 10

Pro Ser Phe Pro Asn Leu Gly Arg Pro Ala Leu Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: isoform eIF4G

<400> SEQUENCE: 11

Pro Ser Phe Asp Asn Leu Gly Arg Pro Ala Leu Ser
1               5                   10

<210> SEQ ID NO 12
<211> LENGTH: 18
<212> TYPE: DNA
<213> ORGANISM: Artificial Sequence
<220> FEATURE:
<223> OTHER INFORMATION: TALEN portion

<400> SEQUENCE: 12
ccgtcctttg ccaacctt                                                   18

<210> SEQ ID NO 13
<211> LENGTH: 18
<212> TYPE: DNA
<213> ORGANISM: Artificial Sequence
<220> FEATURE:
<223> OTHER INFORMATION: TALEN portion

<400> SEQUENCE: 13
agcaaccgtg ggccccca                                                   18

<210> SEQ ID NO 14
<211> LENGTH: 16
<212> TYPE: DNA
<213> ORGANISM: Artificial Sequence
<220> FEATURE:
<223> OTHER INFORMATION: TALEN portion

<400> SEQUENCE: 14
tggccgacca gccctt                                                     16

<210> SEQ ID NO 15
<211> LENGTH: 15
<212> TYPE: DNA
<213> ORGANISM: Artificial Sequence
<220> FEATURE:
<223> OTHER INFORMATION: TALEN portion

<400> SEQUENCE: 15
cccaaggggt gggcc                                                      15

<210> SEQ ID NO 16
<211> LENGTH: 73
<212> TYPE: DNA
<213> ORGANISM: Artificial Sequence
<220> FEATURE:
<223> OTHER INFORMATION: portion of EIF4GI gene
```

```
<400> SEQUENCE: 16
cagacttcac tccgtccttt gccaaccttg gccgaccagc ccttagcaac cgtgggcccc        60 caagggtgg gcc                                                            73

<210> SEQ ID NO 17
<211> LENGTH: 73
<212> TYPE: DNA
<213> ORGANISM: Artificial Sequence
<220> FEATURE:
<223> OTHER INFORMATION: EIF4GI gene portion isoform

<400> SEQUENCE: 17
cagacttcac tccgtccttt gccgacttcg gccgaccagc ccttagcaac cgtgggcccc        60 caagggtgg gcc                                                            73

<210> SEQ ID NO 18
<211> LENGTH: 90
<212> TYPE: DNA
<213> ORGANISM: Artificial Sequence
<220> FEATURE:
<223> OTHER INFORMATION: EIF4GI gene portion

<400> SEQUENCE: 18
cccagacttc actccgtcct ttgccgactt cggccgacca gcccttagca accgtgggcc        60 cccaagggt gggccaggtg gggagctgcc                                          90
```